(12) United States Patent
Vilasi et al.

(10) Patent No.: US 11,590,307 B2
(45) Date of Patent: Feb. 28, 2023

(54) EXPANDABLE INTER VIVOS TUBE

(71) Applicants: Joseph A. Vilasi, Bradenton, FL (US); Joseph D'Ambrosio, Ridgefield, CT (US)

(72) Inventors: Joseph A. Vilasi, Bradenton, FL (US); Joseph D'Ambrosio, Ridgefield, CT (US)

(*) Notice: Subject to any disclaimer, the term of this patent is extended or adjusted under 35 U.S.C. 154(b) by 0 days.

(21) Appl. No.: 17/585,294

(22) Filed: Jan. 26, 2022

(65) Prior Publication Data

US 2022/0409838 A1    Dec. 29, 2022

Related U.S. Application Data

(60) Provisional application No. 63/215,477, filed on Jun. 27, 2021.

(51) Int. Cl.

| A61M 16/04 | (2006.01) |
|---|---|
| A61M 25/04 | (2006.01) |
| A61M 5/00 | (2006.01) |
| A61M 29/00 | (2006.01) |
| A61M 25/00 | (2006.01) |

(52) U.S. Cl.
CPC ............ A61M 16/044 (2013.01); A61M 5/00 (2013.01); A61M 16/0431 (2014.02); A61M 16/0475 (2014.02); A61M 25/04 (2013.01); A61M 29/00 (2013.01); A61M 25/0023 (2013.01); A61M 2025/0024 (2013.01); A61M 2025/0035 (2013.01)

(58) Field of Classification Search
CPC .. A61M 2025/0024; A61M 2025/0035; A61M 5/00; A61M 25/0023; A61M 2025/0025; A61M 25/04; A61M 29/00; A61M 16/044; A61M 16/0431; A61M 16/0475
USPC ...................................................... 128/207.15
See application file for complete search history.

(56) References Cited

U.S. PATENT DOCUMENTS

| 2,116,426 | A | * | 5/1938 | Cecil | ...................... | E01C 13/00 |
|---|---|---|---|---|---|---|
| | | | | | | 52/103 |
| 2,438,140 | A | * | 3/1948 | Auten | ...................... | E04B 2/62 |
| | | | | | | 52/464 |
| 3,039,649 | A | * | 6/1962 | Aleck | ..................... | H02G 9/065 |
| | | | | | | 220/684 |
| 3,085,301 | A | * | 4/1963 | Nuorivaara | ............. | E04F 19/06 |
| | | | | | | 52/471 |
| 3,968,800 | A | | 7/1976 | Vilasi | | |

(Continued)

*Primary Examiner* — Justine R Yu
*Assistant Examiner* — Alexander Morales
(74) *Attorney, Agent, or Firm* — Law Office of Carl Giordano, PC

(57) ABSTRACT

An expandable inter-vivos tube that allows for the use in medical procedures while limiting known complications arising from conventional inter-vivos tubes is presented, wherein the expandable inter-vivos tube comprises a slit formed longitudinally within a tube and a plurality of nipples extending from an outer surface of the tube that are insertable within a corresponding one of a plurality of slides within an outer slidable element that is slidable within the slit. A position of the nipples within the slots causes a distance between the edges of the to increase; thus, increasing a circumference of the inter-vivos tube as the outer element is slide from a proximal end of the tube element to a distal end of the tube.

18 Claims, 18 Drawing Sheets

(56) References Cited

U.S. PATENT DOCUMENTS

| | | | |
|---|---|---|---|
| 4,084,066 A * | 4/1978 | Gillemot | H02G 15/10 |
| | | | 138/158 |
| 4,755,335 A | 2/1988 | Vilasi | |
| 4,777,072 A * | 10/1988 | Cason, Jr. | F16L 9/17 |
| | | | 24/615 |
| 4,827,925 A | 5/1989 | Vilasi | |
| 5,579,762 A | 12/1996 | Lee | |
| 5,647,358 A | 7/1997 | Vilasi | |
| 6,729,334 B1 * | 5/2004 | Baran | A61M 16/0463 |
| | | | 128/207.14 |
| 8,413,659 B2 | 4/2013 | Crumback | |
| 8,807,136 B2 * | 8/2014 | O'Neil | A61M 16/0484 |
| | | | 128/207.14 |
| 9,010,332 B2 | 4/2015 | Vilasi | |
| 9,107,577 B2 | 8/2015 | Vilasi | |
| 10,016,575 B2 * | 7/2018 | Vazales | A61M 25/1002 |
| 10,391,272 B1 * | 8/2019 | Vilasi | A61M 16/0418 |
| 10,688,287 B2 * | 6/2020 | Pedroni | A61M 25/0668 |
| 10,722,322 B2 * | 7/2020 | Vazales | A61M 16/0418 |
| | | | 128/207.14 |
| 2014/0238405 A1 * | 8/2014 | Vilasi | A61M 16/0816 |
| | | | 128/207.14 |
| 2015/0224282 A1 * | 8/2015 | Christiansen | A61M 25/0668 |
| | | | 604/164.01 |

* cited by examiner

EXPANDABLE INTER VIVOS TUBE

CLAIM OF PRIORITY

This applicant claims, pursuant to 35 USC 119, priority to and the benefit of the earlier filing date of that provisional patent application filed on Jun. 27, 2021 and afforded Ser. No. 63/215,477, the contents of which are incorporated by reference, herein.

FIELD OF INVENTION

This invention is related to the field of medical devices and more particularly, to expandable inter-vivo tubes and means for controlling their expansion.

BACKGROUND OF THE INVENTION

Inter-vivos or endotracheal tubes (ETTs) tubes, when inserted in a patient, are used to provide an air passage to sedated patients, who may not be able to ventilate autonomously. Conventional ETT (consisting of a long hollow tube with an inflatable cuff balloon near the distal end) are sized according to their internal diameter (ID). In children the ID varies from 3.5 to 7 mm (millimeters) and in adults, typical, tube size range from 7 to 11 mm. The selection of the size of the tube to be used to intubate a patient is based on the experience of the practitioner, wherein the practitioner selects the largest ID tube that may be inserted through the glottis (vocal cord) region into the trachea.

However, the selection of too small a tube creates a restricted gas flow, which is especially detrimental if a patient is ventilating spontaneously in the operating room, in intensive care unit and elsewhere.

Hence, the size of a selected ETT is based on characteristics of the patient (e.g., male/female, adult/child, etc.) and the experience of the person performing the insertion raises issues regarding whether the selected ETT is the proper size for the patient.

Furthermore, after selecting a correct ETT circumference size in relation to the glottic size, conventional ETTs include an intramural canal constructed within the wall of the ETT which leads on an inflatable cuff balloon near the distal end of the tube. The exposed outer end of this canal is connected to a one-way valve and syringe to inflate the balloon. The inflatable cuff balloon of present day ETT compensates for any mis-sizing of a selected ETT by expanding, through the introduction of air through the intramural canal, the distal end cuff balloon to press the cuff balloon against the tracheal wall.

Once, confirmation of a leak free contact within the trachea is made, the patient is ready for the delivery of anesthetic gases and oxygen.

However, the expanded distal cuff balloon pressing against the trachea wall compresses delicate tracheal wall capillaries, which may rupture and case internal damage.

Thus, the (ischemic) compression of tracheal wall capillaries often results in the inflammation of the tracheal wall, diminished capillary activity and causing, in cases, Ventilator Associated Pneumonia (VAT), all of which being well-known and documented issues arising from using conventional ETTs Another drawback of conventional ETTs is that the walls of the conventional ETT, which are generally 1.5 mm thick, are sized to accommodate the intramural canal within the ETT wall that is required to provide a passageway to inject air into the cuff balloon.

A still further drawback of conventional ETTs is the length to which the ETT are manufactured so as to pass the vocal cords and extend into the trachea. For example, in a six-foot male, the distances from lips to vocal cords is 6.25 inches and nose to vocal cords is 7.5 inches. However, conventional ETTs are generally in the order of 11.8 inches in length, which h contributes to ventilatory dead space.

Hence, there is need in the industry of an expandable ETT that overcomes the drawbacks of present-day ETT design.

SUMMARY OF THE INVENTION

It is an object of the instant invention to provide a new and inventive design for an expandable inter-vivos tube and a corresponding expansion control element design that is applicable to the inter-vivos tubes that allows for the expansion/contraction of the tube without incurring the problems of conventional ETTs.

In one aspect of the invention, an expandable inter-vivos tube is constructed with at least one slit extending along a longitudinal axis of a tube element. Each of the at least one slit forming opposing edges that substantially abut one another when in the closed position. The tube element, which is composed of known material (e.g., human gradable flexible plastic) similar to materials used in conventional inter-vivos tubes, is suitable for insertion through the vocal cord region with minimal insertion into the trachea.

On opposing sides of the at least one slit and on an outer surface of the tube element are a plurality of nipples substantially proximate to a corresponding slit. Further disclosed is a slidable element positioned within a corresponding one of the at least one slit, which includes a plurality of slots into which a corresponding one of the plurality of nipples extends. As the slidable element is slide within a corresponding slit, the position of the nipples within a corresponding slit causes a distance between the edges of the corresponding slit to expand and, thus, increase a diameter of the inter-vivos tube.

In one aspect of the invention, the slidable element, associated with each of the at least one slit, extends above a proximal end of the inter-vivos tube and is slidable toward a distal end of the tube element.

In accordance with another aspect of the invention, the edges of the slidable element may include a flexible membrane that reduces the sharpness of the edges to allow for a smoother movement of the slidable element.

In accordance with another aspect of the invention, an intramural channel is incorporated into a wall of the tube element, which connects to an expandable cuff balloon element is positioned toward the distal end of the tube element. The expandable cuff balloon operates to contact the fibrous vocal cord region to fill gaps that may occur between the expand tube element and the vocal cords.

In accordance with a still further aspect of the invention, an expansion control element may be configured to engage a proximal end of the slidable element to allow for the movement of the slidable element within a corresponding slit by the application of a downward force onto the slidable element.

In accordance with a still further aspect of the invention, the expansion control element may include a nipple configured to engage an L-shaped notch within the slidable element, wherein the engage nipple allow for both the expansion of a contracted tube element by applying a pushing force to the expansion control element and contraction of an expanded tube element by applying a pulling force to the expansion control element.

In another aspect of the invention, a flange may be incorporated substantially near a proximal end of the inter-vivos tube element to allow for the application of an upward force to be applied to the tube element as a downward force is applied to the expansion control element.

In accordance with a second exemplary embodiment of the invention, the tube element includes a plurality of channels into which the slidable element is positioned.

In accordance with a third exemplary embodiment of the invention, the tube element includes a plurality of channels wherein each of the channels includes a pocket into which the edges of the slidable element are inserted.

BRIEF THE DESCRIPTION OF THE FIGURES

For a better understanding of exemplary embodiments and to show how the same may be carried into effect, reference is made to the accompanying drawings. It is stressed that the particulars shown are by way of example only and for purposes of illustrative discussion of the preferred embodiments of the present disclosure and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. It would be understood that the drawings are not drawn to scale. In the accompanying drawings:

The figures and descriptions of the present invention described herein have been simplified to illustrate the elements that are relevant for a clear understanding of the present invention, while eliminating for purposes of clarity, many other elements. However, because these omitted elements are well-known in the art, and because they do not facilitate a better understanding of the present invention, a discussion of such elements is not provided herein. The disclosure herein is directed also to variations and modifications known to those skilled in the art.

DETAILED DESCRIPTION OF THE INVENTION

Figure 1:
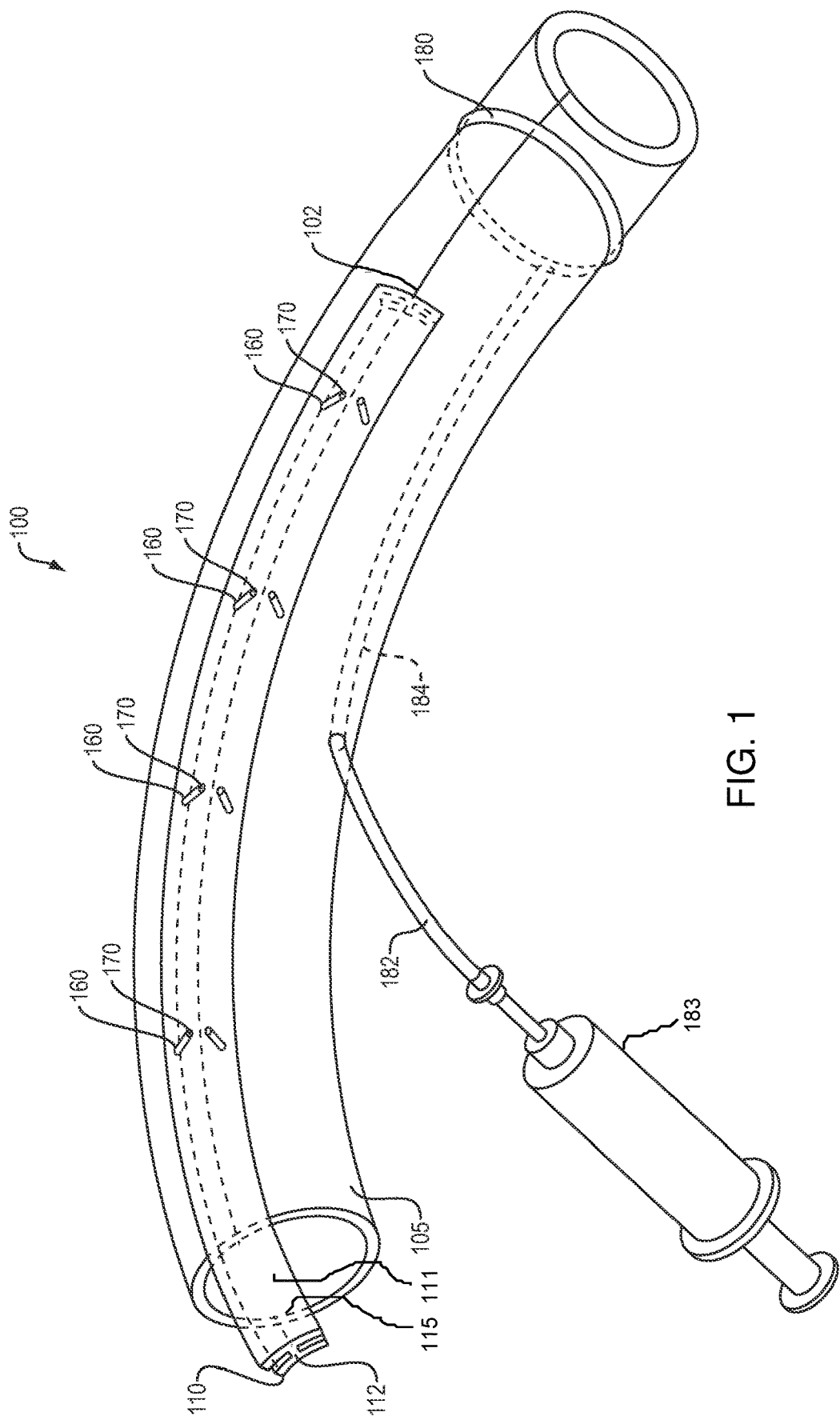
FIG. 1 illustrates a prospective view of a first exemplary embodiment of an inter-vivos tube in accordance with the principles of the invention.

FIG. 1 illustrates a prospective view of the first exemplary embodiment of an inter-vivos tube 100 in accordance with the principles of the Invention.

In this illustrated first exemplary embodiment, inter-vivos tube 100 comprises a tube member 105 including a slit 102 along a longitudinal axis of tube member 105, which divides tube element 105 into two parts.

Further illustrated is expansion element 111 including outer member 115, inner member 110 and joining element 112, which is positioned within slit 102. In this illustrated initial position, wherein slit 102 is in a substantially closed position (i.e., minimum internal diameter (ID) of tube element 105 (a proximal end of expansion element 11 is shown positioned above a proximal end of tube element 105. As showed expander element 111 extends toward a distal end of tube element 105.

Further illustrated are nipples 170 formed on an outer surface of tube element 105 and a plurality of slots 160 within outer member 1115. In this illustrated example, four slots 160 are positioned on each side of slit 112. However, it would be understood that the number of slots 160 (and nipples 170) may be increased or decreased without altering the scope of the invention. Furthermore, as shown, in this closed position of tube element 105, nipples 170 are positioned at a distal end of a corresponding one of slots 160.

Further illustrated, and in an alternative aspect of the invention claimed, is distal end expandable cuff balloon 180, which may be expanded by the use of syringe element 183 that may inject air through tubes 182 and intramural tube 184 that is positioned within a wall of tube element 105.

Figure 1A:
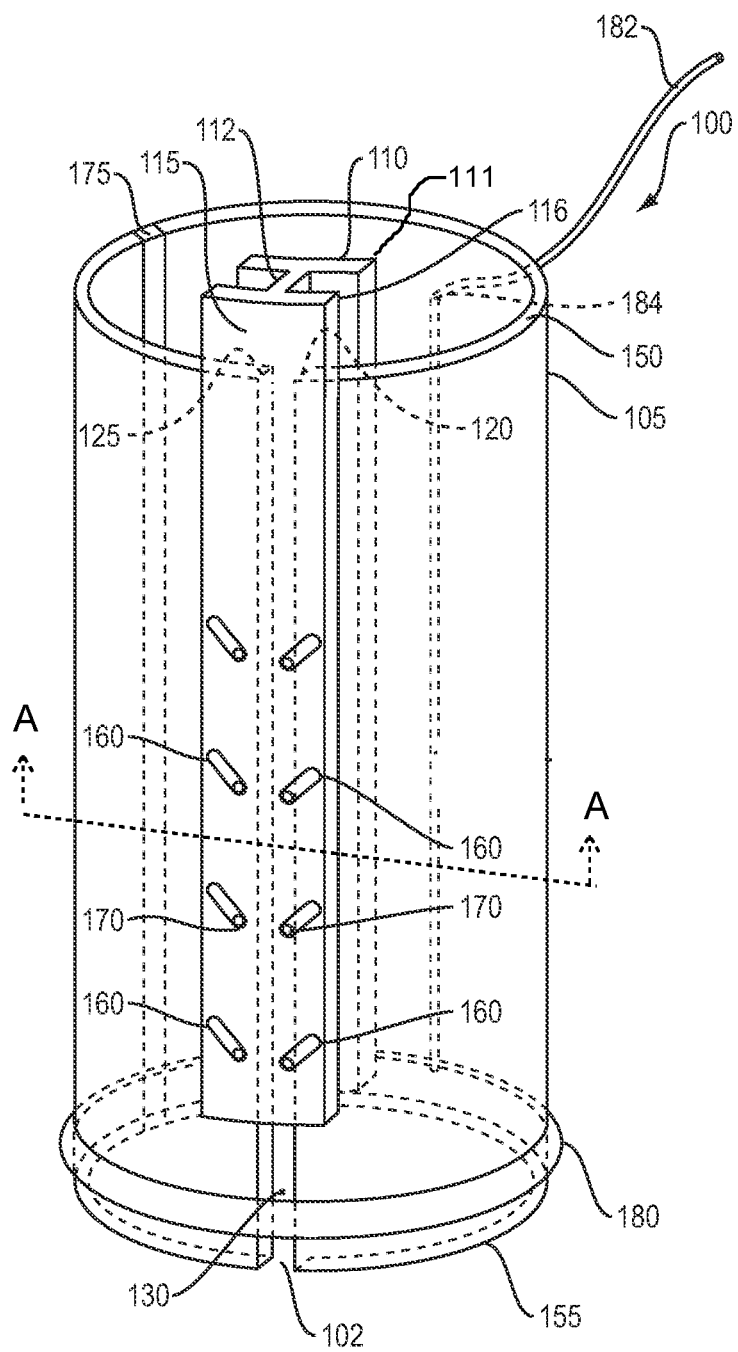
FIG. 1A illustrates a prospective view of a first aspect of the first exemplary embodiment of an inter-vivos tube in accordance with the principles of the invention.

FIG. 1A illustrates in further detail a prospective view of a first aspect of the first exemplary embodiment of an inter-vivos tube 100 shown in FIG. 1.

In this illustrated embodiment, a tube element 105 includes at least one slit 102 (of which only one is shown) that extends along the longitudinal axis of the tube element 105. Slit 102 creates a first longitudinal tube edge 120 and a second longitudinal tube edge 125. Further illustrated an expansion element 111 inserted into slot 102. Expansion element 111 comprises an outer member 115 external to, and positioned along, an outer circumference of tube element 105 covering slit 102 and an inner member 110 internal to, and along an inner circumference of tube element 105 covering slit 102. The outer member 115 and inner member 110 extend from proximal end 150 of tube element 105 to a position substantially close to, but not in contact with distal end 155 of tube 105. For example, a distal end of outer member 115 and distal end of inner member 110 may be initially positioned 1-1.5 inches above the distal end 155.

In accordance with the principles of the invention, the limited length of inner member 110 and outer member 115 creates a space 130 near the distal end 155 of tube 100 that allows gases injected into inter-vivos tube 100 to exit both t distal end 155 and space 130.

Expansion element 111 further comprises joining member 112 extending from substantially a mid-point on an outer surface of inner member 110 through slit 102 to substantially a mid-point on an inner surface of outer member 115. Joining member 112 causes inner member 110 and outer member 115 to operate as a single unit as expansion element 111 is slide downward.

In this illustrated example, slit 102 is shown in a contracted configuration, wherein edges 120 and 125 are substantially adjacent to one another and a proximal end 116 of outer member 115 (and inner member 110) extends above proximal end 150 of tube element 105.

Further illustrated are a plurality of slots 160 arranged diagonally within outer member 115.

The plurality of slots 160 are diagonally positioned from proximate to slit 102 and extend upwardly toward proximal end 116 away from slit 102.

Within each of the slots 160 is shown a nipple (or tab) element 170 positioned at a distal end of a corresponding one of the slots 160. Nipples 170, which are positioned substantially adjacent to slit 102, extend from an outer surface of tube element 105.

Although four slots 160, on either side of slit 102, are shown extending from slit 102 are shown, it would be recognized that the number of slots 160 distributed along the longitudinal axis of tube 105 may be increased or decreased without altering the scope of the invention claimed.

Further illustrated is the previously discussed (and optional) distal end cuff balloon that is configured to expand an inserted inter-vivos tube 100 to seal any gaps that may exist between the expanded inter-vivos tube 100 and a vocal cord region.

Intramural tube element 184, which, as in conventional inter-vivos tubes, may be contained within a wall of tube element 105 to inject air (or fluid) into distal cuff balloon 180. Air may be supplied to distal end cuff balloon 182 through tube element 182, as is known in the art.

Further illustrated is an exemplary optical path 175 within a wall of tube element 105 that extends from a proximal end 150 of tube element 105 to a distal end 155 of tube element 105. Optical path 175 comprises an optically clear material that allows light injected into proximal end 150 to be transferred to distal end 155, Although optical path 175 is shown as a discrete element, it would be recognized that tube element 105 may be made of an optically transparent material, which would allow the passage of light injected into proximal end 150 to be transferred to distal end 155. Similarly, optical path 175 may be incorporated into outer member 115, connector 112 or inner member 110 without undue experimentation.

As would be recognized, tube element 105 and members 110, 112 and 115 may be constructed from medically approved materials that are suitable for usage with people.

Figure 1B:
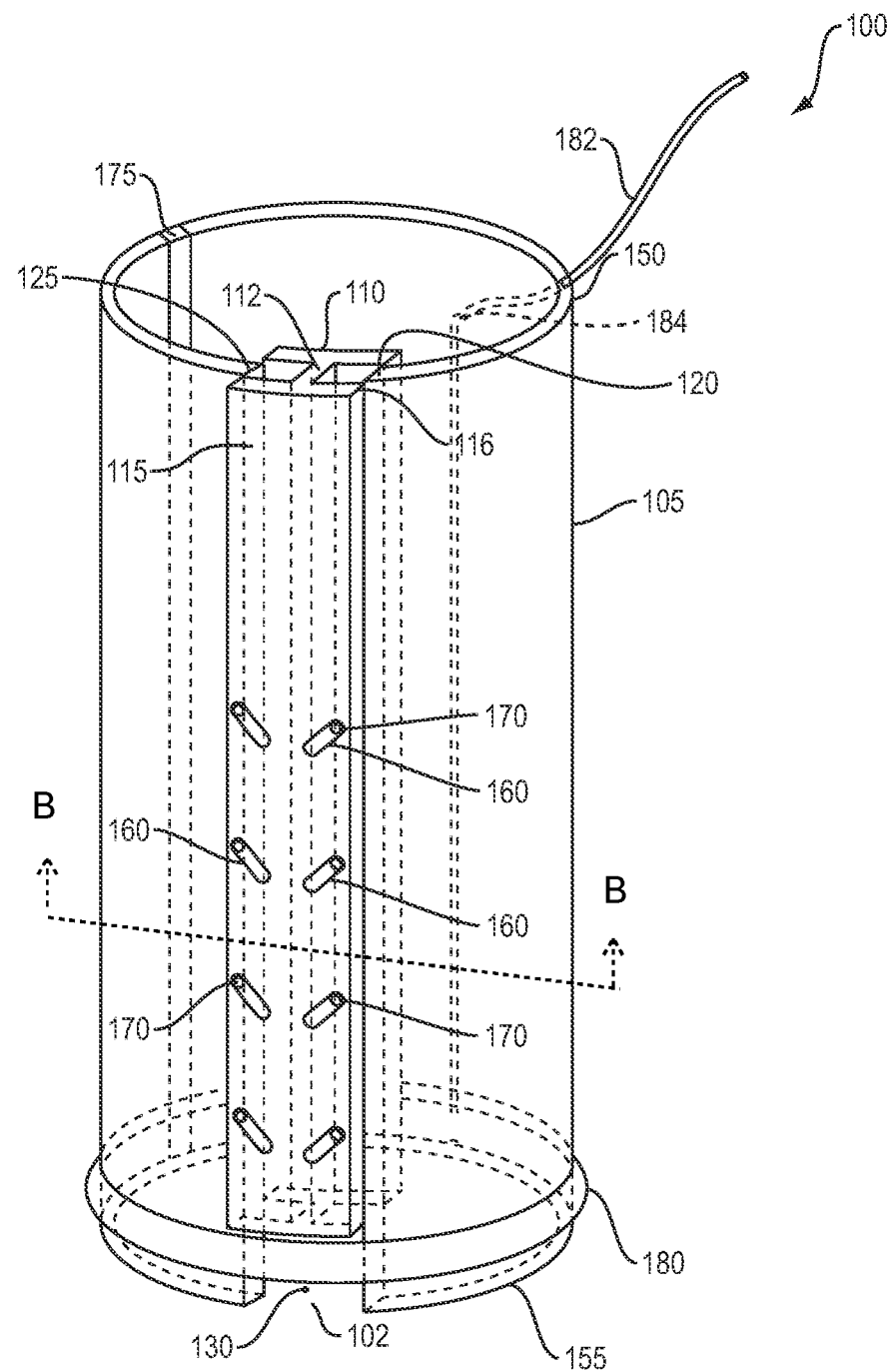
FIG. 1B illustrates a prospective view of a second aspect of the first exemplary embodiment of an inter-vivos tube in accordance with the principles of the invention.

FIG. 1B illustrates a second aspect of the exemplary first embodiment of an inter-vivos tube 100, shown in FIG. 1, in accordance with the principles of the invention.

In this illustrated aspect, control element 111 (i.e., outer member 115 and inner member 110 is slide downward, such that the proximal end 116 of outer member 115 is substantially flush with proximal end 150 of tube element 105. That is, maximum expansion of inter-vivos tube 100.

Although maximum expansion is illustrated, it would be recognized that expansion of inter-vivos tube 100 continuously increased from the minimum configuration shown in FIG. 1A to the maximum configuration shown in FIG. 1B, wherein the expansion configuration is limited to the size of the glottis (vocal cord) region.

That is, as control mechanism 111 (i.e., outer member 115) is moved downward from the initial position shown in FIG. 1A, the nipples (or tabs) within slots 160 move within slots 160 to spread apart the edges 120, 125 of slit 102.

In accordance with the principles of the invention, the increase in the space between edges 120, 125 causes an increase in the circumference of inter-vivos tube 100, such that the increased tube size contacts the vocal cords (not shown) to provide a seal between inter-vivos tube 100 and the vocal cords (not shown). This seal enables a practitioner to begin the process of injecting air or gases into the patient.

Figure 1C:
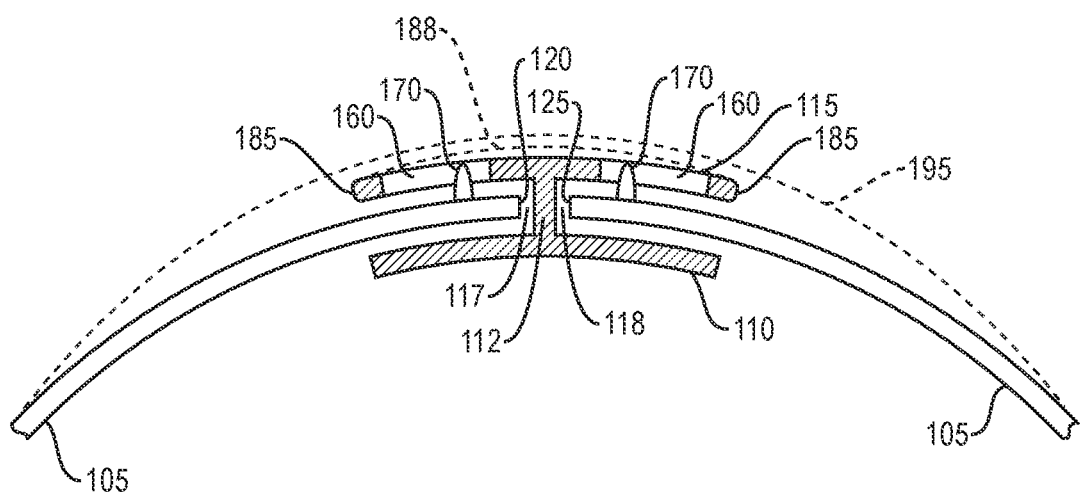
FIG. 1C illustrates a cross-sectional view, through section A-A of the exemplary embodiment shown in FIG. 1A.

FIG. 1C illustrates a cross-sectional view, through section A-A of the exemplary embodiment shown in FIG. 1A.

As shown outer member 115, inner member 110, and connector 112, inserted through slot 102, form pockets 117, 118 on both sides of connector 112, into which edges 120, 125 of slit 102 of tube element 105 are inserted.

Further illustrated are slots 160 within outer member 115 wherein nipples or tabs 170 formed on an outer surface of tube element 105 are positioned.

Further illustrated is edge covering 185 applied to edges of outer member 115. Edge covering 185 provides for the smooth movement of outer member 115 and to prevent damage that may be caused by a sharp edge of outer member 115. Edge coverings 185 may be formed from a silicon type material, for example, which is appropriate for medical usage.

Further illustrated is an optional flexible membrane 188 that extends across the outer member 115 from one edge to another edge. Flexible membrane 188 provides a smooth surface to outer member 115 while retaining nipples 170 within slots 160.

Further illustrated is a second optional flexible outer membrane 195 that encompasses tube element 105. Flexible outer membrane 195 provides for a smooth outer surface of inter-vivos tube 100 and for further protection from sharp edges of outer member 115.

Figure 1D:
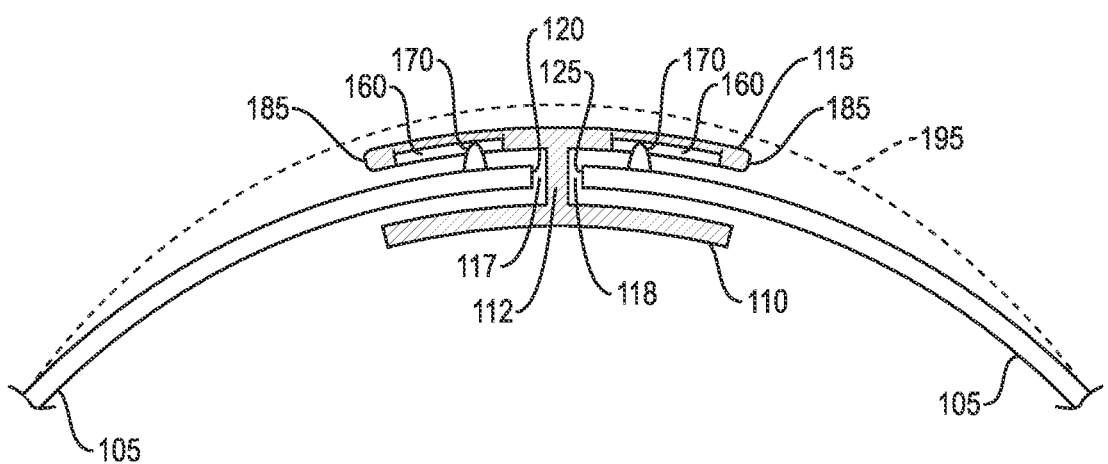
FIG. 1D illustrates a cross-sectional view, through section A-A of a second aspect of the exemplary embodiment shown in FIG. 1A

FIG. 1D illustrates a cross-sectional view, through section A-A of a second aspect of the exemplary embodiment shown in FIG. 1A.

Similar to the configuration shown in FIG. 1C, FIG. 1D illustrates an alternative configuration wherein slots 160 are represented as pockets within outer member 115 into which nipples 170 are inserted.

In this exemplary alternative configuration, the sliding of nipples 170 within pockets 160 is retained within outer member 115 to provide a smooth transition as nipples 170 slide within slots (pockets) 160.

Figure 1E:
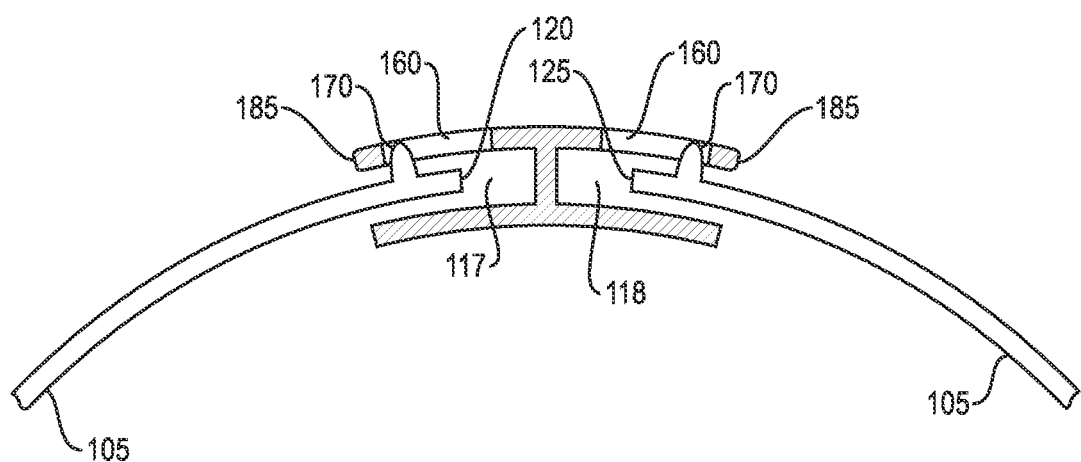
FIG. 1E illustrates a cross-section view, through section B-B- of the exemplary embodiment shown in FIG. 1B.

FIG. 1E illustrates a cross-section view, through section B-B, of the second aspect of inter-vivos tube 100 shown in FIG. 1B.

In this illustrated aspect, wherein outer member 115 is slide downward, nipples or tabs 170 are shown at a proximal end of slot 160 and a distance between edges 120 and 125 is increased.

Figure 2A:
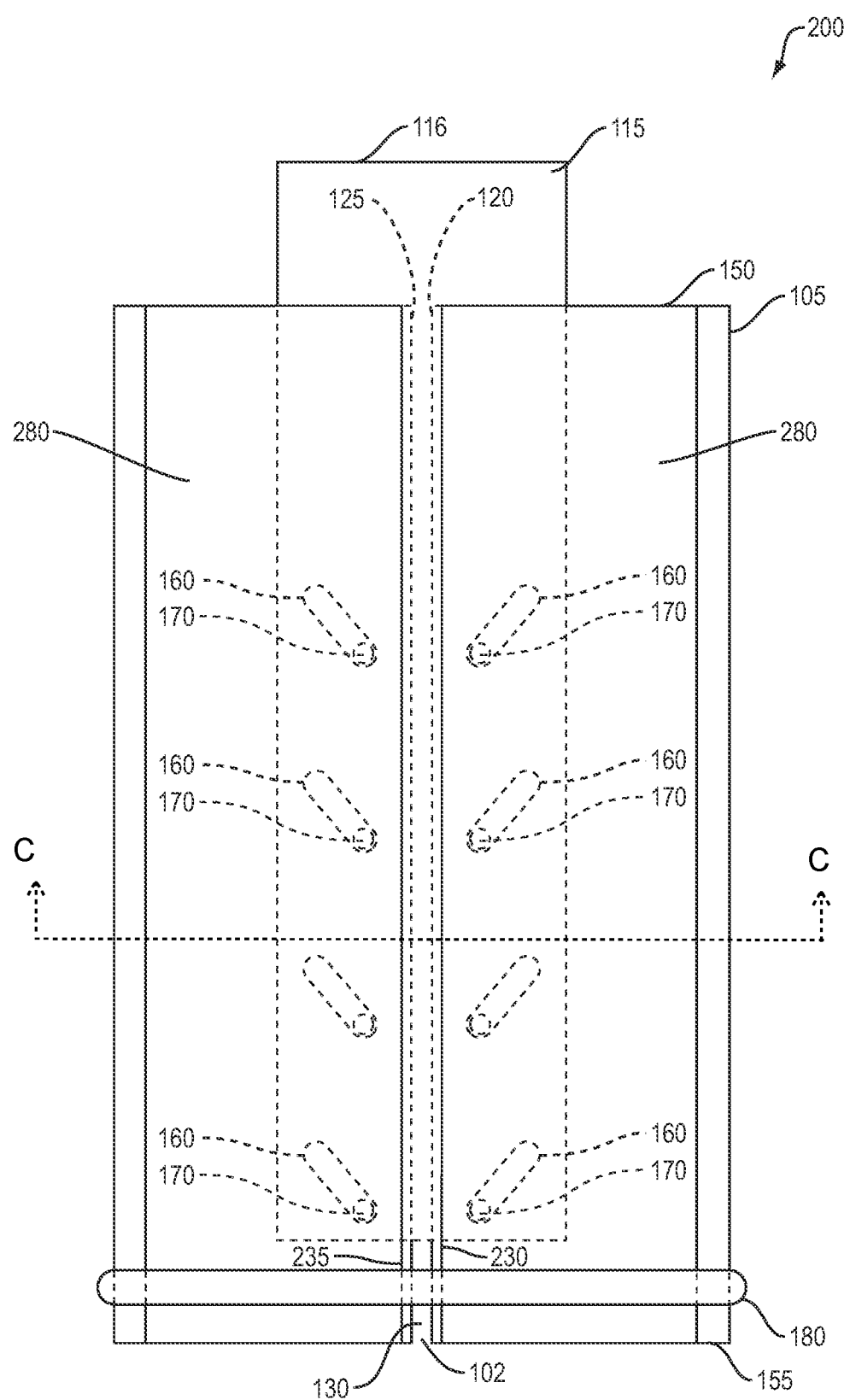
FIG. 2A illustrates a front view of a first aspect of a second exemplary embodiment of an inter-vivos tube in accordance with the principles of the invention.

FIG. 2A illustrates a front view of first aspect of a second exemplary embodiment of an inter-vivos tube 200 in accordance with the principles of the invention In this exemplary embodiment, inter-vivos tube 200 similar to inter-vivos tube 100 includes at least one slit 102, an inner member 110 (not shown), an outer member 115 and a joining element 112 (not shown). Further illustrated are slots 160 and nipples 170, wherein nipples or tabs 170 are positioned at a distal end of a corresponding one of slots 160.

Further illustrated are extension members 280 extending from an outer surface of tube 105 toward respective edges 230, 235 from proximal end 150 to distal end 155. Extension members 280 create a channel (not shown) into which outer member 115 is movable within. Although extension members 280 are shown extending from proximal end 150, it would be recognized that extension members 280 may be formed along a portion of tube element 105 wherein the not shown channels are of sufficient length to contain the entire movement of outer member 115.

In this illustrated case, slots 160 and nipples 170 are shown as dotted lines as these elements are positioned behind extension member 280.

Figure 2B:
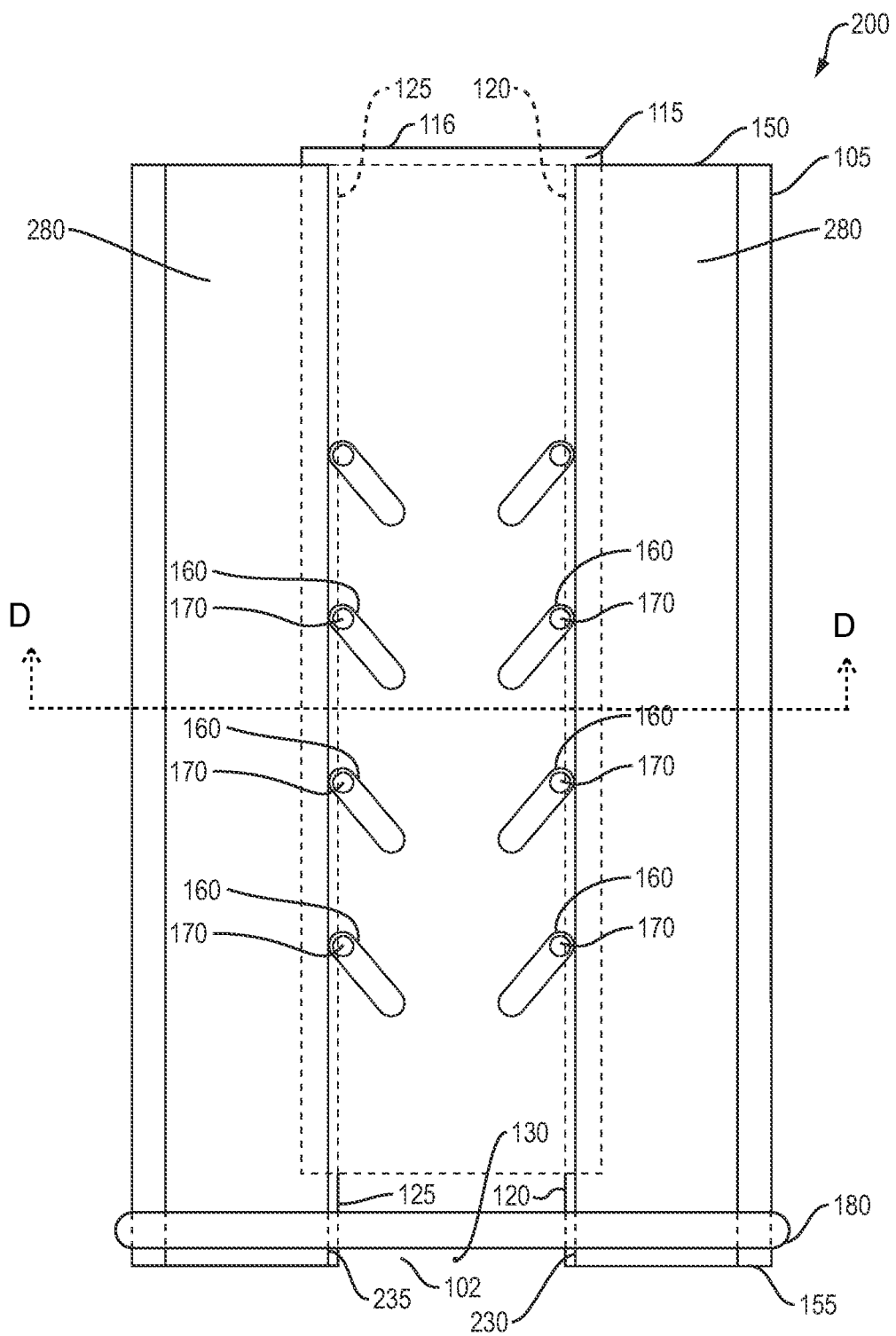
FIG. 2B illustrates a front view of a second aspect of the second exemplary embodiment of the inter-vivos tube shown in accordance with the principles of the invention.

FIG. 2B illustrates a front view of a second aspect of the second exemplary embodiment of the inter-vivos tube shown in FIG. 2A.

In this illustrated second aspect of inter-vivos tube 200, wherein inter-vivos tube 200 is shown in the maximum, extended position, outer membrane 115 (and inner member 110 through connection 112) is positioned proximal to proximal end 150 of tube 105. Furthermore, nipples 170, which were shown at a distal end of a corresponding slot 160 in the contracted position shown in FIG. 2A, are shown substantially adjacent a proximal end of slots 160 of FIG. 2B.

Thus, as expansion element 111 (i.e., outer member 115 and inner member 110) are moved downward, the position of nipples 170 within slots 160 move from a distal end of slot 160 to a proximal end of slot 160 (wherein proximal end of slot 160 is closest to proximal end 150 of tube element 105.

In this illustrated configuration, inter-vivos tube 200 is at a maximum expansion as nipples 170 are shown positioned at the distal end of corresponding slots 160.

Figure 3:
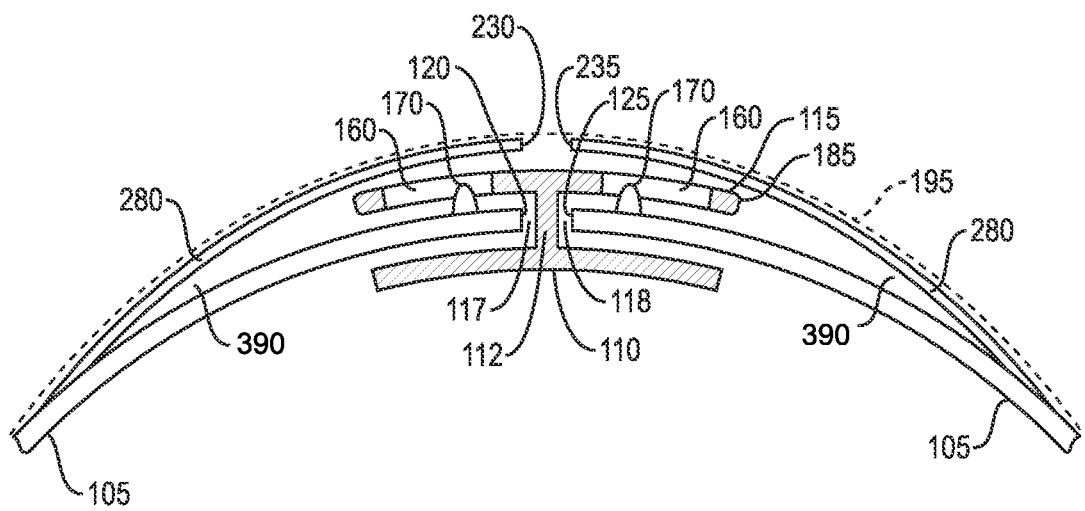
FIG. 3 illustrates a cross-sectional view, through section C-C of the exemplary embodiment shown in FIG. 2A.

FIG. 3 illustrates a cross-sectional view, through section C-C, shown in FIG. 2A, in accordance with the principles of the invention.

In this illustrated cross-sectional view, tube element 105 is positioned within pockets 117, 118 formed by outer member 115, inner member 110 and connecting element 112, as previously discussed. Further illustrated are nipples 170 positioned on an outer surface of tube element 105 and extending outwardly into a corresponding one of slot 160 within outer member 115. Further illustrated are extension elements 280 extending from an outer surface of tube element 105.

In this illustrated case, extension elements 280 are formed conformally to tube element 105 and form channels 390 between the outer surface of tube element 105 and an inner surface of extension element 280. Further shown, are the edges of outer member 115 contained within a flexible membrane 185 to prevent shape edges.

In accordance with the principles of the invention, as outer member 115 is slide downward within channels 390, the tabs 170 move within slots 160 to expand a distance between edges 120, 125.

Further illustrated is the optional outer flexible membrane 195 covering the tube element 105 and extension elements 280. Flexible membrane 195 provides a smooth outer surface of inter-vivos tube 200 that enables a smoother insertion of tube 200 into a patient.

Figure 4:
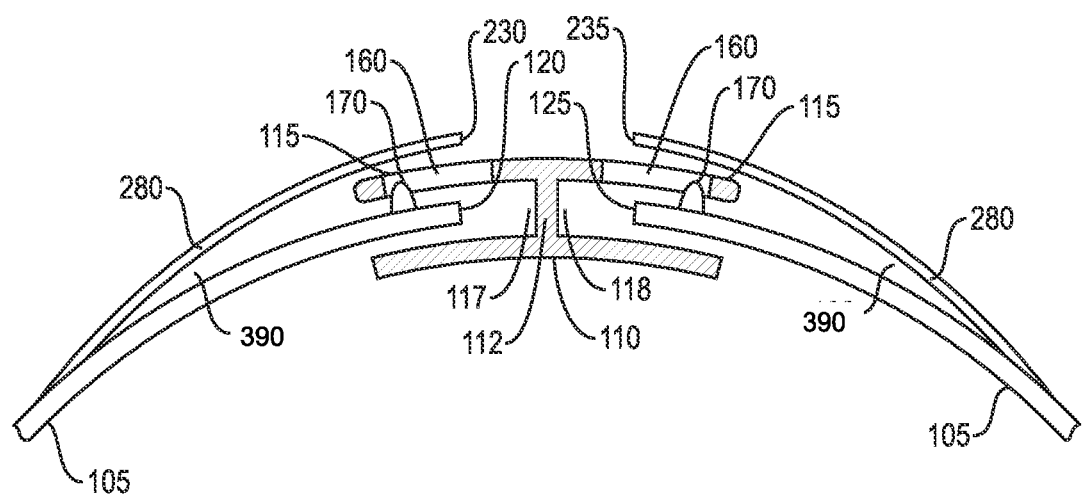
FIG. 4 illustrates a cross-sectional view, through section D-D of the exemplary embodiment shown in FIG. 2B.

FIG. 4 illustrates a cross-sectional view, through section D-D shown in FIG. 2B, wherein slit 102 is expanded to a maximum extent by the movement of outer element 115 through channels 390 causing tabs 170 on outer surface of tube element 105 to move between a distal end of slot 160 to a proximal end of slot 160.

Figure 5:
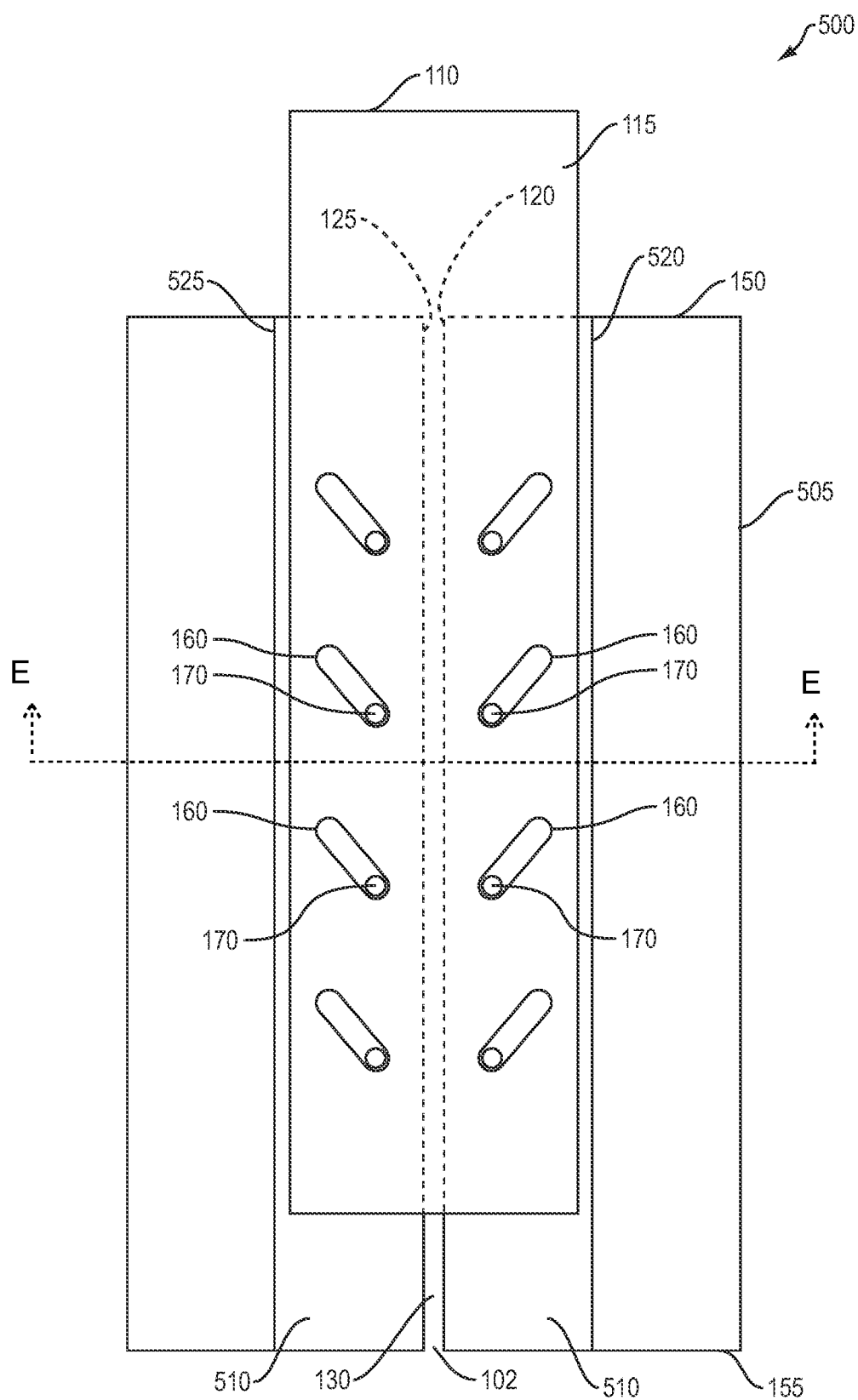
FIG. 5 illustrates a front view of a first aspect of a third exemplary embodiment of an inter-vivos tube in accordance with the principles of the invention.

FIG. 5 illustrates a front view of a first aspect of a third exemplary embodiment of an inter-vivos tube 500 in accordance with the principles of the invention.

In this third exemplary embodiment, inter-vivos tube 500 comprises tube element 505 comprising a slit 102 along a longitudinal axis of tube element 505 similar to the slit 102 disclosed with regard to FIG. 1A.

Further illustrated are edges 120, 125 of slit 102, wherein slit 102 is in a substantially closed or contracted (minimum expansion) position. Further illustrated is outer member 115 extending across slit 102. Outer member 115 further includes slots 160 positioned along a longitudinal axis of outer member 115 and extending diagonally upwardly from a position proximate to silt 102.

In accordance with the principles of this third exemplary embodiment of the invention, a channel 510 is formed within tube element 105 on each side of slit 102, wherein outer member 115 is Positioned within and substantially adjacent respective edges 520, 525 formed by channel 510 on each side of slit 102. Channel 510 provides for the partial inclusion of outer member 115 within the body of tube 505 to prevent the edges of outer member 115 from being exposed.

Figure 6:
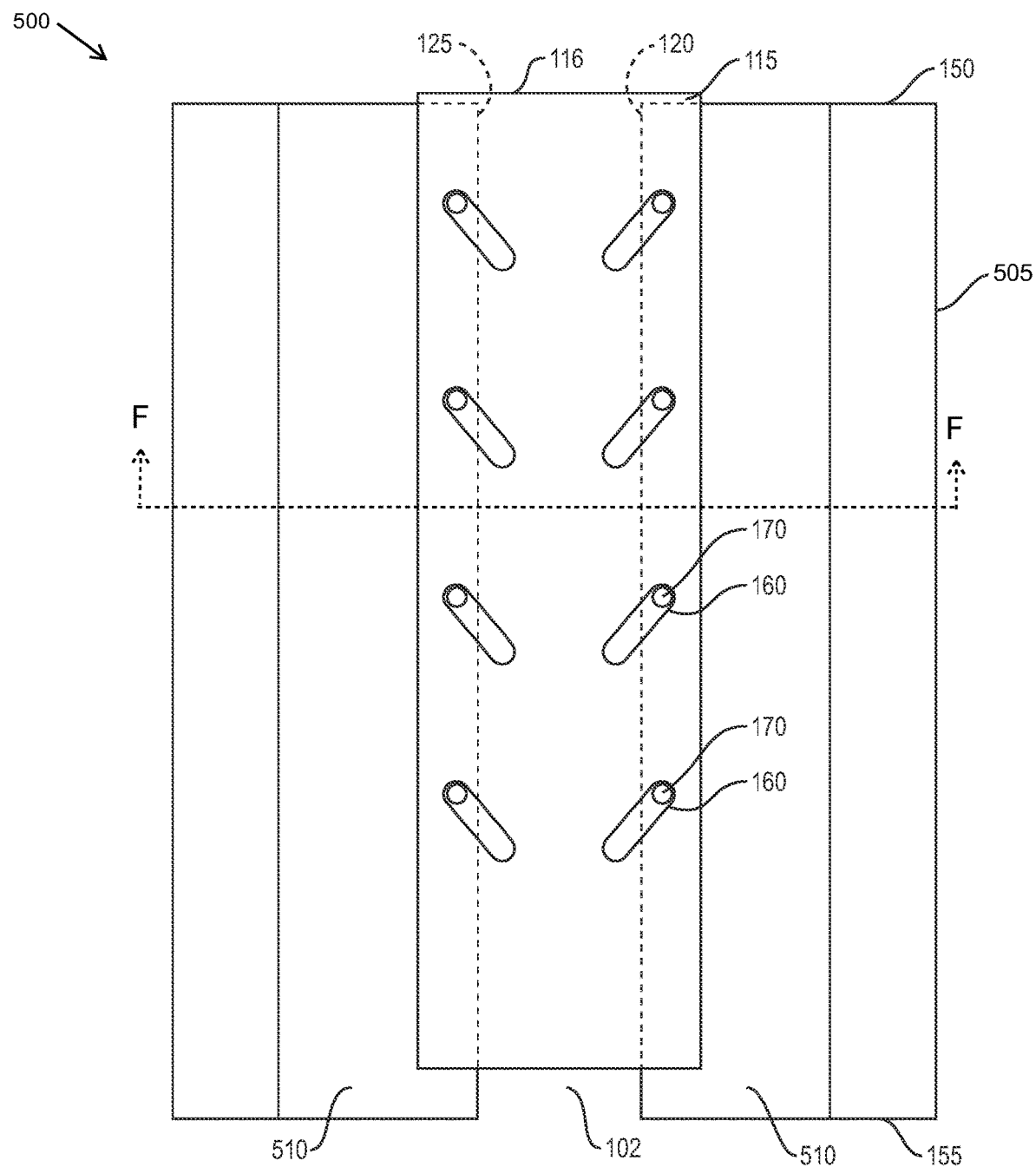
FIG. 6 illustrates a front view of a second aspect of the third exemplary embodiment of the inter-vivos tube shown in FIG. 5.

FIG. 6 illustrates a front view of a second aspect of the third exemplary embodiment of the inter-vivos tube shown in FIG. 5.

In this illustrated second aspect, outer member 115 is shown positioned downward within channels 510 and extending a distance between edges 120, 125, by the movement of tabs 170 within corresponding ones of slots 160, as previously discussed.

Although not shown in FIG. 6, it would be recognized that outer flexible membrane 195 may encapsulate tube element 105 to provide a smooth outer surface of inter-vivos tube 500

Figure 7:
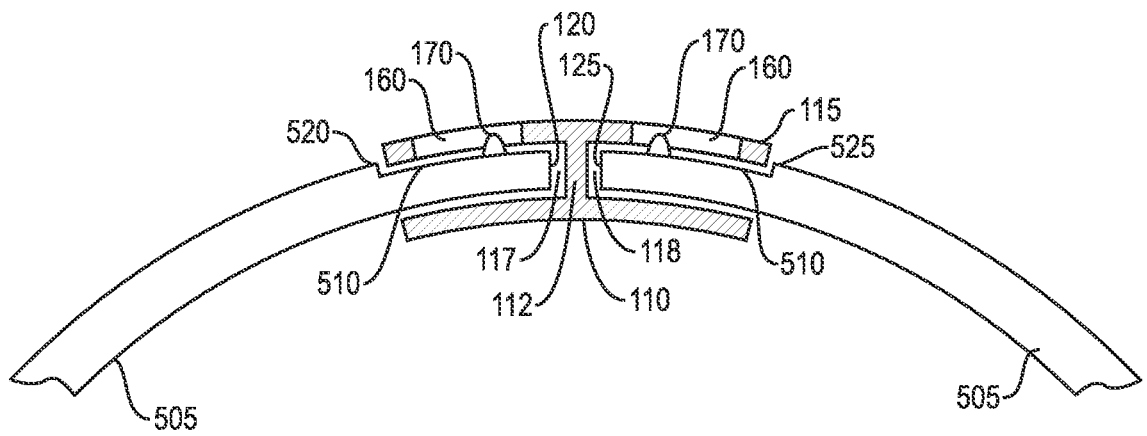
FIG. 7 illustrates a cross-sectional view, through section E-E of the exemplary embodiment shown in FIG. 5.

FIG. 7 illustrates a cross-sectional view, through section E-E, of the inter-vivos tube 500 shown in FIG. 5, wherein inter-vivos tube 505 is shown in a minimum expansion configuration.

In this illustrated view, tube element 505 includes slit 102 and channels or recesses 510 formed on each side of slit 102 wherein nipples 170 extend from an outer surface of tube 510 within channel 510.

In accordance with this third example embodiment, outer member 115 is positioned within channels 510 on each side of slit 102. As shown, outer member 115 is sized in thickness such that an outer surface of outer member 115 is substantially flush (i.e., even, level) to an outer surface of tube element 505 such that a smooth surface is obtained between the outer surface of tube element 505 and the outer surface of outer member 115.

In one aspect of the invention, it would be recognized that the thickness of outer member 115 may be such that the outer surface of outer member 115 may extend past the outer surface of tube element 505.

As previously discussed, nipples 170, extending from an outer surface of tube element 505 (or a lower surface of channel 510) are positioned at a distal end of a corresponding one of slot 160 within outer member 115.

Although not shown, it would be recognized that outer flexible membrane 195 may surround or encapsulate tube element 505 and outer member 115 to provide a smooth external surface for inter-vivos tube 500.

Figure 8:
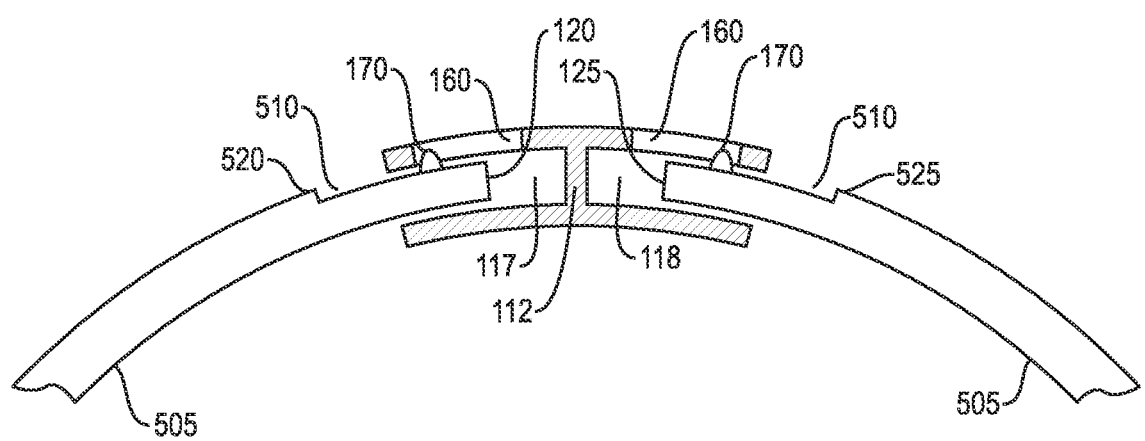
FIG. 8 illustrates a cross-sectional view, through section F-F of the exemplary embodiment shown in FIG. 6.

FIG. 8 illustrates a cross-sectional view, through section F-F, of the inter-vivos tube 500 shown in FIG. 6, wherein outer member 115 is slide downward within channel 510 to cause nipples 170 to slide within slots 160 from a distal position within slot 160 (FIG. 5) to a proximal position within slot 160 (FIG. 6), as previously discussed.

As shown, the positional change of tabs 170 within corresponding slots 160 causes edges 120, 125 of slit 102 to separate and expand the circumference of tube element 505.

Although not shown, it would be recognized that an outer flexible membrane 195 may surround tube element 505 and outer member 115 to provide a smooth external surface for inter-vivos tube 500.

Figure 9:
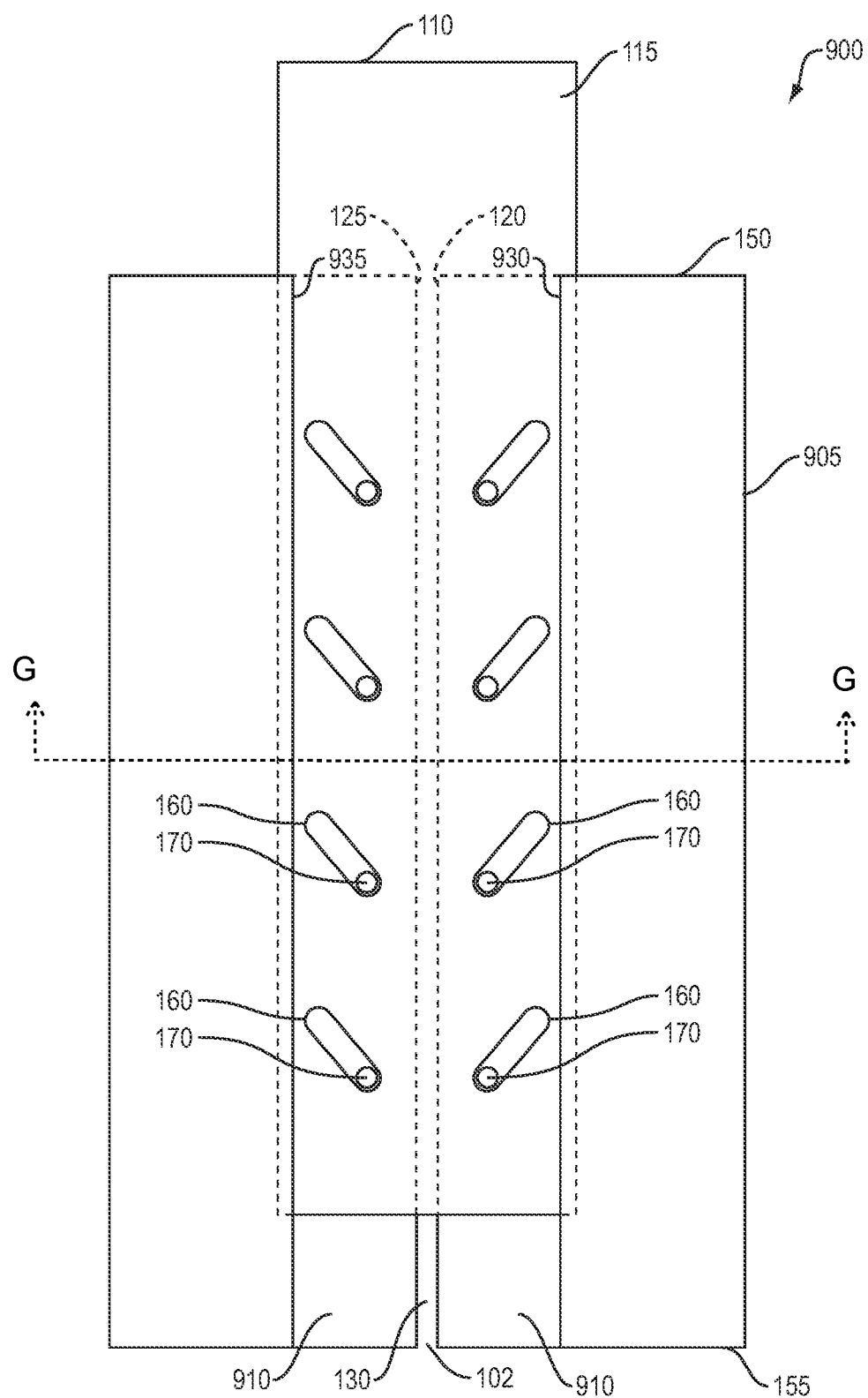
FIG. 9 illustrates a front view of a fourth exemplary embodiment of the inter-vivos tube in accordance with the principles of the invention.

FIG. 9 illustrates a front view of a first aspect of a fourth exemplary embodiment of an inter-vivos tube 900, in accordance with the principles of the invention.

Inter-vivos tube 900, similar to inter-vivos tubes 100 (FIG. 1), 200 (FIG. 2) and 500 (FIG. 5) includes tube element 905 including slit 102 extending along a longitudinal axis of tube element 905 and channels 510, similar to those shown in FIG. 5, formed on each side of slit 102. Insertable and slidable within channels 510 is outer member 115 which is joined to not shown inner member 110 through connector 112.

Within outer member 115 are slots 160, extending diagonally along outer member 115 and within each of slots 160 is nipple 170, as previously discussed.

Further illustrated are channel 910 formed within tube element 905. Channel 910 is constructed to contain the outer edges of outer member 115 when is in the illustrated initial position.

Accordingly, as outer member 115 is slide from the illustrated initial position toward distal end 155 of tube element 905, tabs 170 within slots 160 move from the illustrated distal end of slot 160 to a proximal end of slot 160. The shifted position of nipples 170 within slots 160 causing slit 102 to open, as discussed with regard to the previously embodiments of the invention disclosed, herein.

Figure 10:
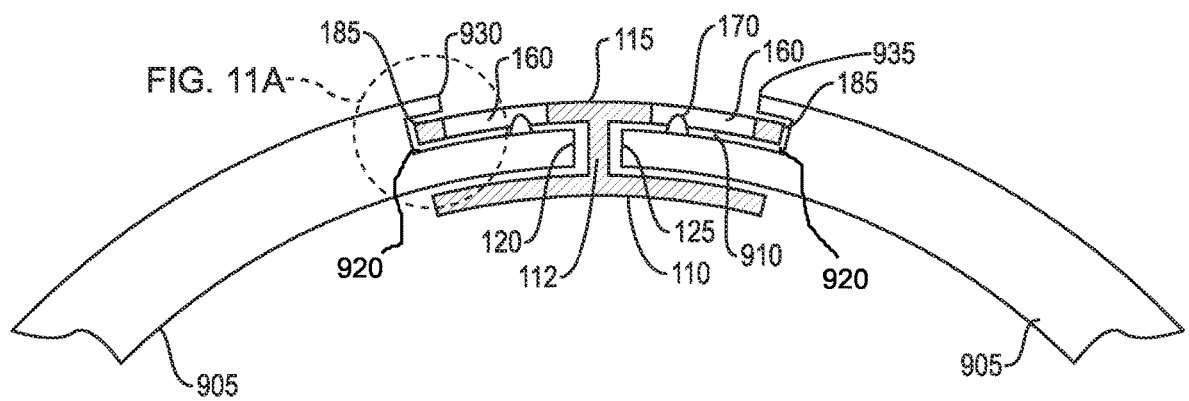
FIG. 10 illustrates a cross-sectional view, through section G-G, of the configuration of the fourth exemplary embodiment of an inter-vivos tube shown in FIG. 9.

FIG. 10 illustrates a cross-sectional view, through section G-G of FIG. 9, comprising tube element 905 including slit 102 and channels 910 on each side of slit 102 with nipples 170 extending or protruding into slots 160 of outer member 115.

Further illustrated are pockets 920 including edges 930, 935, which are formed within tube element 905 into which the outer edges of outer element 115 may be inserted. Further illustrated is flexible element 185 positioned on each of the outer edges of outer element 115.

In this exemplary configuration, outer element 115 slidable, longitudinally, within channel 910 while being retained within pocket 920 as outer element 115 is slide downward toward distal end 155 of tube element 905.

Although not shown, it would be recognized that tube element 905 may be surrounded or enclosed within an outer flexible membrane 195, which provides a substantially smooth outer surface for inter-vivos tube 900.

Figure 11A:
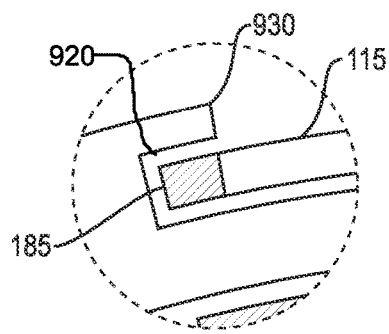
FIG. 11A Illustrates expanded view of a first aspect of the area identified as FIG. 11A shown in FIG. 10.

FIG. 11A illustrates an expanded view of the area designed as FIG. 11A in FIG. 10 wherein an outer edge of outer element 115 is shown retained within pocket 920, wherein pocket 920 is formed between an outer surface of tube element 905 and an outer surface of channel 910.

Figure 11B:
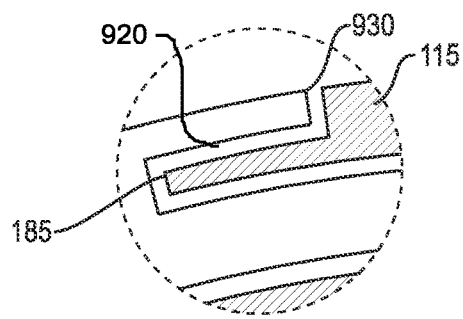
FIG. 11B illustrates an expanded view of a second aspect of the area identified as FIG. 11A shown in FIG. 10.

FIG. 11B illustrates an expanded view of the area designed FIG. 11A in FIG. 10, wherein edge of outer element 115 is shaped to conform to pocket 920. That is, a thickness of an area about edge of outer member 115 is less than a thickness of outer element 115 such that the outer edge may be insertable (and slidable, longitudinally) within pocket 920.

Figure 12:
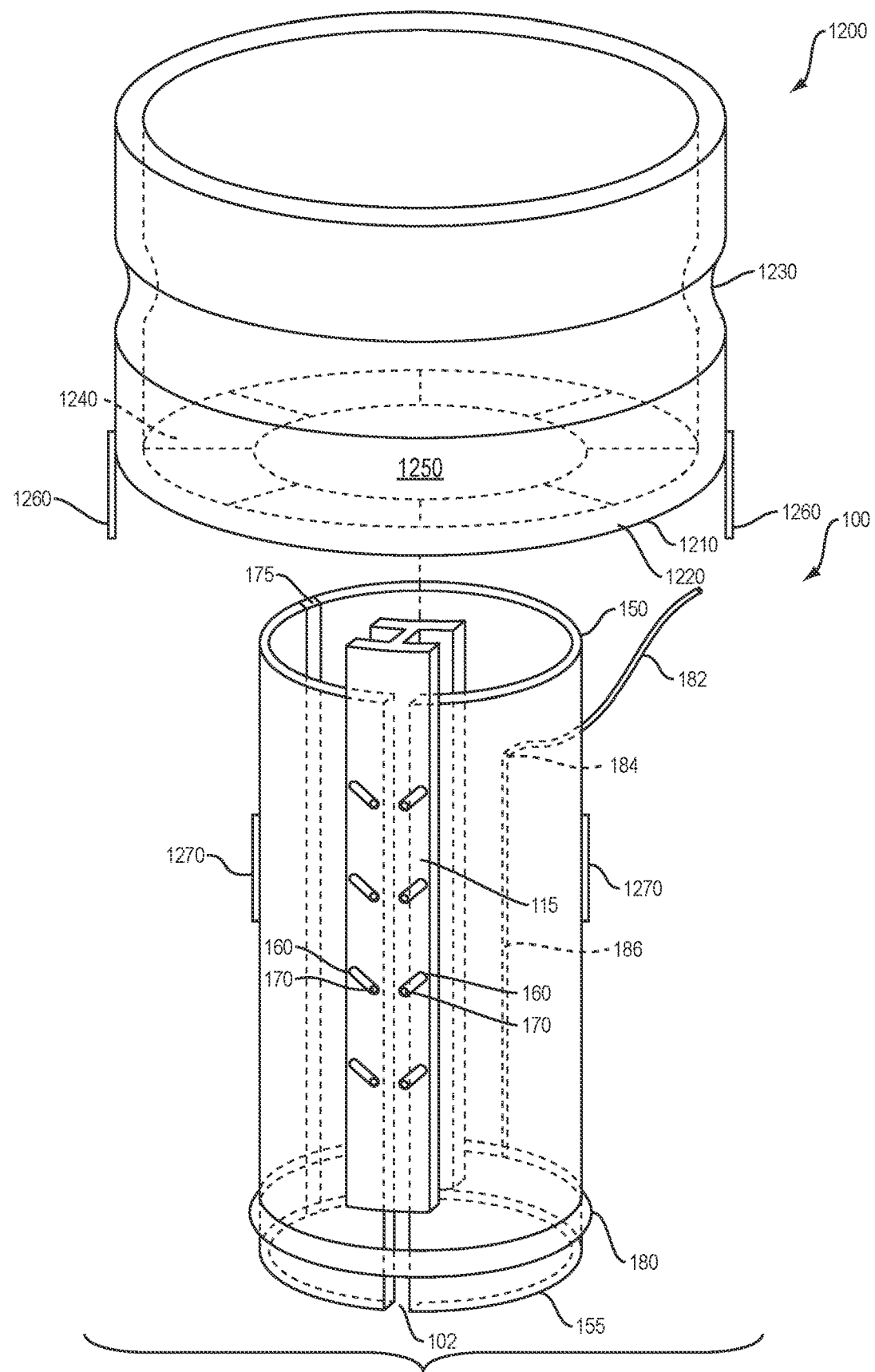
FIG. 12 illustrates a first aspect of a first exemplary embodiment of a control mechanism for controlling the expansion of the embodiments of an inter-vivos tube presented herein.

FIG. 12 illustrates an exemplary embodiment of an inter-vivos tube system 1200 for controlling the expansion of inter-vivos tube 100 (500, 900) disclosed in accordance with the principles of the invention.

In this illustrated embodiment, inter-vivos tube 100, for example, which is discussed and shown in FIG. 1A, is in its initial or contracted configuration wherein a distance between edges 120, 125 of slit 102 is in a minimum, non-overlapping, or abutting, state (i.e., distance substantially zero).

Further illustrated is expansion control unit 111 (i.e., outer element 115, inner element 110 and joining element 112) extending above a proximal end 150 of tube element 105, wherein outer element 115 includes slots 160 into which nipples 170 are shown.

Further illustrated is expansion control element 1220, which is fitted over the proximal end 150 of tube element 105 and is sized to accommodate a full expansion of inter-vivos tube 100.

Expansion control element 1220 comprises an expandable membrane 1240 (i.e., a diaphragm) positioned at, and spanning a distal end 1210 of expansion control element 1220 and an open proximal end 1215, which is sized to accommodate a conventional air supply line. Flexible membrane 1240 includes an opening 1250 into which inter-vivos tube 100 may be inserted. Flexible membrane 1240 provides for a substantially air tight fit between expansion control element 1220 and inter-vivos tube 100 as inter-vivos tube 100 is expanded by the depression of expansion control element 1220 onto expansion element 111.

In accordance with the principles of the invention, the expansion control element 1220 may be composed of a rigid or semi-rigid material or an expandable material that allows for an increase in the size of the expansion control element 1220 as the size of tube element 105 is increased.

Further illustrated is indenture 1230 within expansion control element 1220. Indenture 1230 provides for an area or region that narrows the passage within expansion control element 1220 to control the movement of expansion control element 1220 with respect to outer member 115.

As expansion control element 1220 is pushed onto control element 111 (and tube element 105), applied downward force causes control element 111 to move downward with respect to tube element 105, which causes nipples or tabs 170 within slots 160 correspondingly move from their position at a distal end of a correspond slot 160 to a proximal end of the corresponding slot 160. The upwardly moving nipples or tabs 170 cause slit 102 to expand and, thus, increase the circumference of the inter-vivos tube 100.

In this illustrated example, the expansion control element 1220 allows for the connection of a conventional air line through which a gas or air may be provided to an inter-vivos tube 100 inserted into a patient.

In accordance with one aspect of the invention, tube element 100 may include a connection element (e.g., a VELCO strip) 1270 and expansion control element 1220 may include an opposing connection element 1260 that is configured to engage and attach to connection element 1270 to hold expansion control element 1220 securely in place after the inter-vivos tube 100 is expanded.

Figure 13:
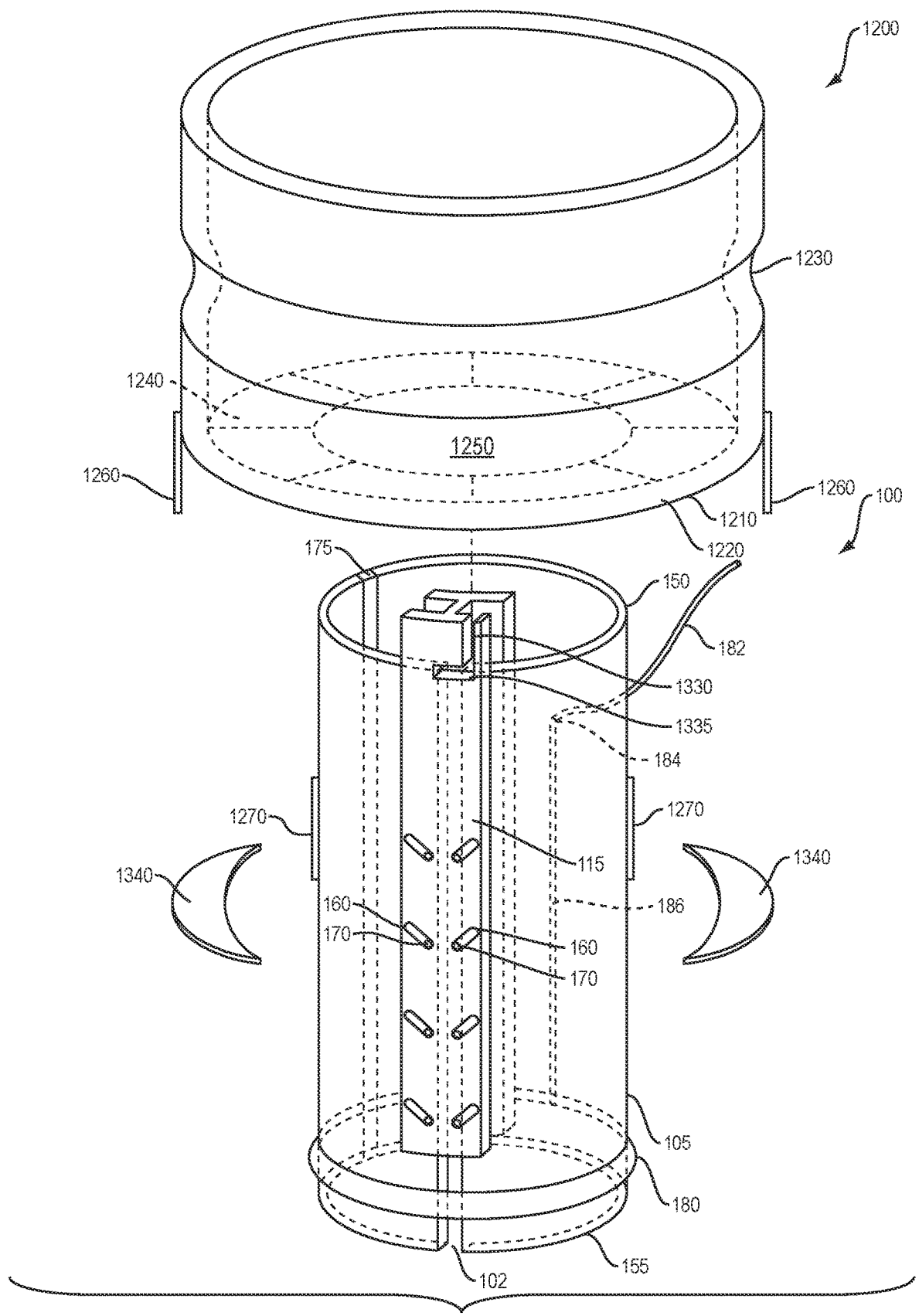
FIG. 13 illustrates a second aspect of the first exemplary control mechanism shown in FIG. 12.

FIG. 13 illustrates a second exemplary embodiment of an inter-vivos tube system 1300 for controlling the expansion of inter-vivos tube 100 (500, 900) disclosed in accordance with the principles of the invention.

Tube system 1300, similar to the tube system 1200 shown FIG. 12, comprises an expansion control means 1220 comprising a distal end diaphragm 1240 including an opening 1250 into which inter-vivos tube 100 (500, 900) may be inserted. Further illustrated is expander comprising outer member 115 and inner member 110 overlapping slit 102, which extends along a longitudinal axis of tube element 105.

In this illustrated second embodiment, expansion control means 1220 includes protrusion 1310 that is positioned on an interior wall of expansion control means 1220. Protrusion 1310 is configured to engage a "L" shaped notch element comprising a vertical leg 1330 from a proximal end 116 of outer member 115 and a horizontal leg 1335 extending from an end of vertical leg 1330.

In accordance with the principles of the invention, the positioning of protrusion 1330 within the horizontal leg 1335 provides a means for expanding inter-vivos tube 100, for example, by the application of a downward (pushing) force onto the proximal end 116 of outer member 115 and horizontal leg 1335 and contracting inter-vivos tube 100 by the application of an upward (pulling) force applied by protrusion 1310 on horizontal leg 1335.

Further illustrated are a plurality of extensions 1340 extending from tube element 105. Extension 1340 provide a means for holding tube element 105 as expansion control means is pushed onto tube element 105 to expand tube element 105.

Figure 14A:
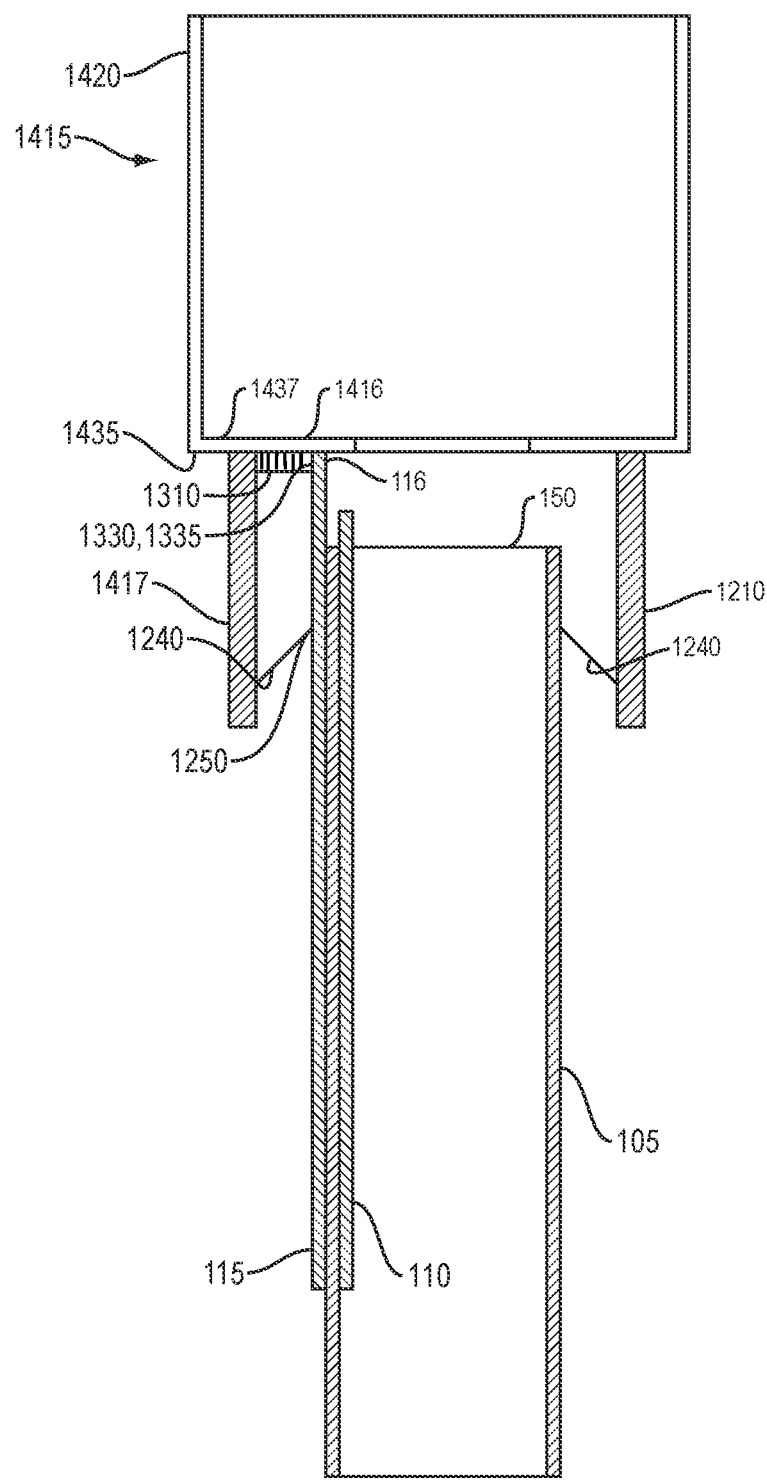
FIG. 14A illustrates a cross-sectional view of a second embodiment of the exemplary control element in accordance with the principles of the invention.

FIG. 14A illustrates a side view of a first aspect of an exemplary inter-vivos tube configuration 1400 comprising a second embodiment of an exemplary expansion control element 1420 and inter-vivos tube 100 (for example) in accordance with the principles of the invention.

In this first aspect wherein inter-vivos tube 100 shown in a minimum ID configuration, wherein outer member 115 (and inner member 110) is positioned above a proximal end 150 of tube element 105.

Expansion control element 1420 comprises a first section 1415, which is sized to accommodate a conventional air-line associated with an air or gas source (not shown), and a second section 1417, which is sized to accommodate a full expansion of inter-vivos tube 100.

Further illustrated is diaphragm 1240 positioned at a distal end 1210 of second section 1417. Diaphragm 1240, as previously discussed, includes an opening 1250 into which inter-vivos tube 100 may be inserted.

First section 1415 comprises a bottom surface 1416 connected to second section 1417, wherein bottom surface 1416 comprises upper surface 1437 and lower surface 1435.

Further illustrated is protrusion 1310 extending from an inner wall of second section 1417 toward outer member 115. In this illustrated case, protrusion 1310 is positioned substantially adjacent to lower surface 1435.

As discussed with regard to FIG. 13, protraction 1310 is insertable into the "L" shaped (i.e., vertical section 1330, horizontal section 1335) notch element within outer member 115 to control the expansion and contraction of inter-vivos tube 100.

In accordance with the principles of the invention, bottom surface 1435 is configured to apply a downward force onto a proximal end 116 to outer member 115 to expand inter-vivos tube 100.

Figure 14B:
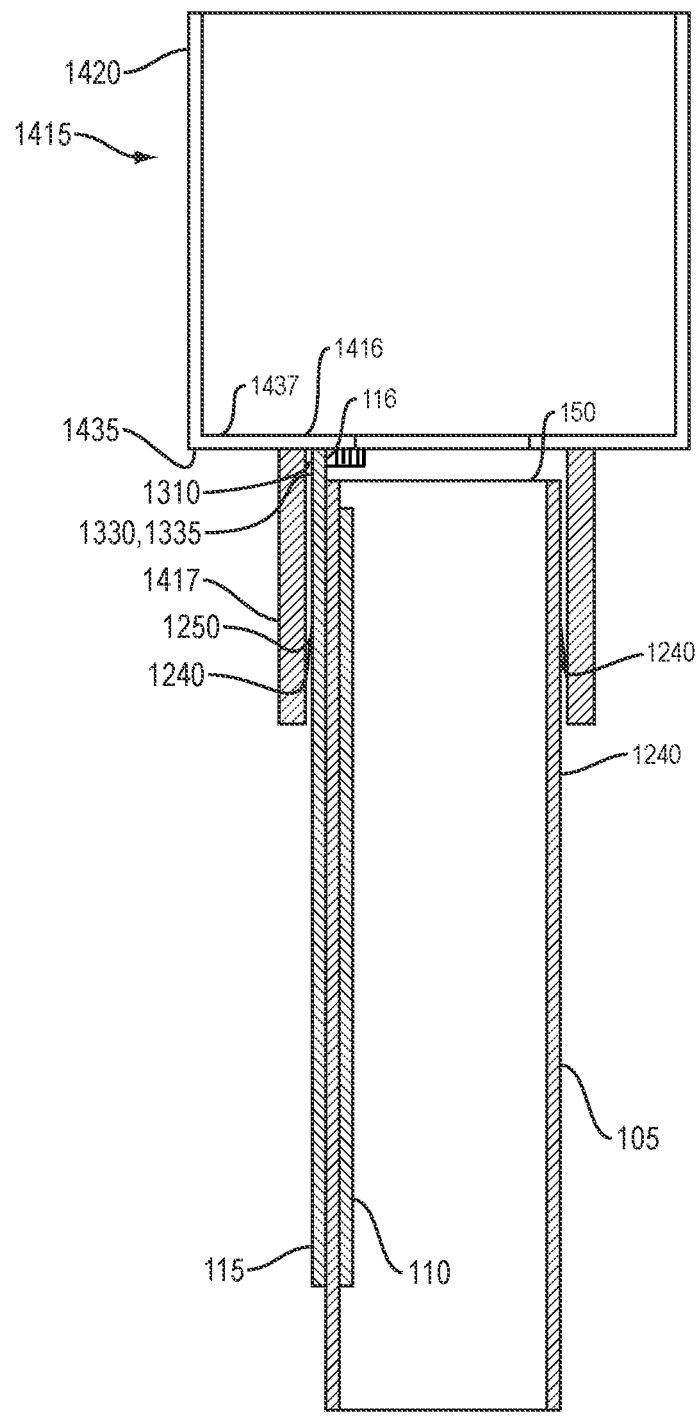
FIG. 14B illustrates a second cross-sectional view of the second embodiment of the exemplary control mechanism shown in FIG. 14B.

FIG. 14B illustrates a side view of a second aspect of an exemplary inter-vivos tube configuration 1400 comprising a second embodiment of an exemplary expansion control element 1420 and inter-vivos tube 100 (for example) in accordance with the principles of the invention.

As shown, the downward force applied by lower surface 1435 to outer member 115 causes outer member 115 and inner member 110 to move downward with respect to inter-vivos tube 100, which causes an expansion of inter-vivos tube 100, as previously discussed.

Figure 15:
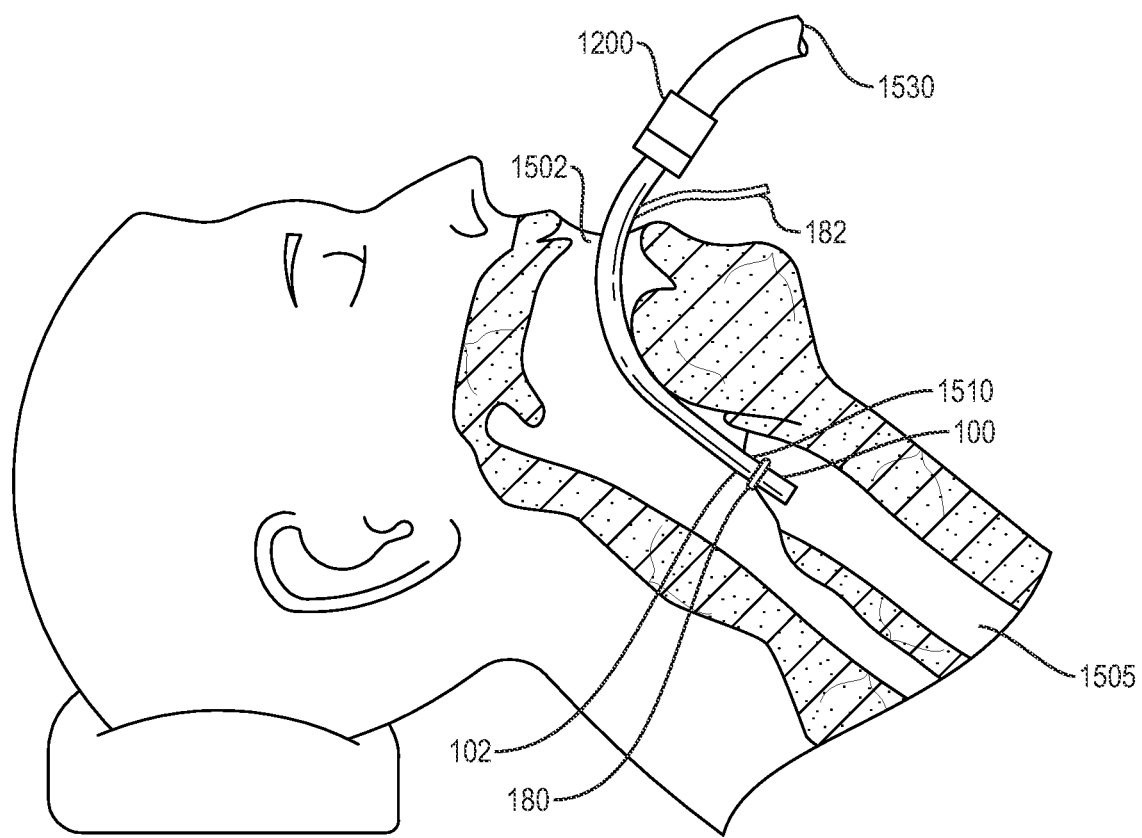
FIG. 15 illustrates a side view of an application of an inter-vivos tube(s) disclosed, herein.

FIG. 15 illustrates an exemplary usage of the inter-vivos tube(s) disclosed, herein, wherein, in this illustrated example, inter-vivos tube 100 is inserted through a patient's mouth 1502 and extends pass the vocal cord region 1510. Once past the vocal cord region 1510, no further extension into the trachea 1505 is necessary to provide anesthesia gas or air to the patient illustrated, as the expansion of inter-vivos tube 100, in accordance with the principles of the invention, contacts the vocal cords 1310 to seal off the patient's breathing. This represents a significant improvement over conventional inter-vivos tubes that require further extension into the trachea 1505 (i.e., increased length of conventional ETTs) and the required expansion of a distal end cuff balloon to contact the sensitive walls of trachea 1505.

Further illustrated is slit 102 on the convex side of inter-vivos tube 100 for the expansion of inter-vivos tube 100 to contact vocal cord region 1510.

Further illustrated is expansion control element 1220 (1420) that provides a connection between inter-vivos tube 100 with a gas flow cable 1530 that may be connected to a conventional anesthesia gas or air supply (not shown).

Although inter-vivos tube 100 is discussed with regard to the expansion control element 1220, it would be recognized that the expansion control element 1220 (1420) would be applicable of any of the inter-vivos tube configurations disclosed, herein.

In one aspect to the invention, a width of outer element 115 may be determined based on the desired expansion of the illustrated inter-vivos tube discussed, herein.

For example, with a minimum inner diameter of 6 millimeter (mm) the circumference of inter-vivos tube is approximately 18 mm. With a desired maximum expansion to 9 mm, the circumference of inter-vivos tube expanses to 28 mm. Hence, slit 102 is required to expand approximately 10 mm. In this case, outer element 115 may be sized to be approximately 10.5 mm to accommodate the required expansion.

As would be recognized, inner elements 110 and outer element 115 may be composed of a flexible or semi-flexible material that allows for the manipulation and flexing of inter-vivos tubes disclosed, herein, during the insertion process.

In summary, an expandable inter-vivos tube 100 is disclosed that comprises a slit 102 formed longitudinally within a tube element 105 and an outer member 115 and an inner member 110, each extending from a proximal end 150 of the tube element 105 to a position above the distal end 155 of the tube element 105.

Positioned within a slit formed along a longitudinal axis to tube 105 is a joining element that joins outer member 115 with inner member 110, wherein outer member includes a plurality of slots arranged along a longitudinal axis of outer member 115. Each of the plurality of slots is oriented diagonally with respect to the longitudinal axis of outer member 115. Within each of the plurality of slots is a nipple formed on an outer surface of tube element 105, wherein the nipples are movable within a corresponding slot as the outer member if forced in a downward direction toward the distal end of tube element 105. The movement of the nipples within a corresponding slot causes the slit 102 to expand and, thus, increase a diameter of the inter-vivos tube.

Further disclosed is an, optional, outer flexible membrane 195 that surrounds or encapsulates tube element 105, from a proximate end 150 of tube 105 to a near a distal end 155 of tube element 105 that provides for a smooth outer surface of inter-vivos tube and for the prevention of air within the inter-vivos tube from escaping.

Further disclosed is an optional, distal end cuff balloon and intramural channel that may be incorporated onto the inter-vivos tube(s) disclosed, herein, wherein the distal end cuff balloon conforms to the vocal cord region.

Further disclosed is a means to provide to control the expansion of inter-vivos tube(s) disclosed, herein, so as to increase a distance between edges 120, 125 of slit 102.

More specifically, the invention claimed comprises, in one aspect of the invention, a tube element comprising a longitudinal slit extending from a proximal end of said slit to said distal end of said tube element, a slidable expander comprising an outer element, an inner element and a joining element, wherein the outer element includes a plurality of slots positioned longitudinally along the outer element into which a plurality of tabs, formed on an outer surface of tube element are located. The tabs, movable between a first position within a corresponding slot to a second position within a corresponding slot, cause an expansion of the slit and increase in a circumference of the inter-vivos tube.

In accordance with a second exemplary embodiment of an inter-vivos tube is disclosed, wherein the inter-vivos tube comprises a tube element including a slit extending from a proximal end of the tube element to a distal end of the tube element, wherein a channel 510 is formed on each side of the slit 102 An outer element of an expander element is configured to lie within the channels formed on each side of the slit. The outer element includes a plurality of slots positioned along a longitudinal axis of the outer member into which a plurality of tab, formed on a lower surface of channels are inserted. The nipples are movable from a first position within a corresponding one of the plurality of slots to a second position, wherein the movement of the nipples within the slots causes an expansion of the slit and increases a circumference of the inter-vivos tube.

In accordance with a third exemplary embodiment of an inter-vivos tube is disclosed, wherein the inter-vivos tube comprises a tube element including a slit extending from a proximal end of the tube element to a distal end of the tube wherein, wherein a channel is formed on each side of the slit 102. Further formed within the channel is a pocket into which an edge of an outer element 115 of an expander element is insertable and slidable. Further disclosed is an optional flexible membrane that surrounds the inter-vivos tube. The flexible membrane is attached at a proximal end and near the distal end to provide for both a smooth surface to assist in intubation and to retain an airtight seal.

Further disclosed are embodiments of exemplary control mechanisms 1220 (1420) to control the expansion of the exemplary embodiments of an inter-vivos tubes disclosed, herein.

Although the invention has been described with regard an inter-vivos tube, it would be recognized that the term "inter-vivos" is a term of art and refers to a general class of endotracheal tubes (EU) and the invention has been described with reference to specific embodiments. However, it would be understood that the invention disclosed, herein, may be suitable for use with other areas of the medical profession.

One of ordinary skill in the art, however, appreciates that various modifications and changes can be made without departing from the scope of the invention as set forth in the claims. Accordingly, the specification is to be regarded in an illustrative manner, rather than with a restrictive view, and all such modifications are intended to be included within the scope of the invention. Benefits, other advantages, and solutions to problems have been described above with regard to specific embodiments. The benefits, advantages, and solutions to problems, and any element(s) that may cause any benefits, advantages, or solutions to occur or become more pronounced, are not to be construed as a critical, required, or an essential feature or element of any or all of the claims.

As used herein, the terms "comprises", "comprising", "includes", "including", "has", "having", or any other variation thereof, are intended to cover non-exclusive inclusions. For example, a process, method, article, or apparatus that comprises a list of elements is not necessarily limited to only those elements but may include other elements not expressly listed or inherent to such process, method, article, or apparatus. In addition, unless expressly stated to the contrary, the term "or" refers to an inclusive "or" and not to an exclusive "or". For example, a condition A or B is satisfied by any one of the following: A is true (or present), and B is false (or not present); A is false (or not present) and B is true (or present); and both A and B are true (or present).

The terms "a" or "an" as used herein are to describe elements and components of the invention. This is done for convenience to the reader and to provide a general sense of the invention. The use of these terms in the description herein should be read and understood to include one or at least one. In addition, the singular also includes the plural unless indicated to the contrary. For example, reference to a composition containing "a compound" includes one or more compounds. As used in this specification and the appended claims, the term "or" is generally employed in its sense including "and/or" unless the content clearly dictates otherwise.

All numeric values are herein assumed to be modified by the term "about," whether or not explicitly indicated. The term "about" generally refers to a range of numbers that one of skill in the art would consider equivalent to the recited value (i.e., having the same function or result). In any instances, the terms "about" may include numbers that are rounded (or lowered) to the nearest significant figure.

It is expressly intended that all combinations of those elements that perform substantially the same function in substantially the same way to achieve the same results are within the scope of the invention. Substitutions of elements from one described embodiment to another are also fully intended and contemplated.

What is claimed is:

1. An inter-vivos tube comprising:
a tube element comprising:
   a slit extending from a proximal end of said tube element to a distal end of said tube element along a longitudinal axis of said tube element, said slit forming a first edge and an opposing second edge;
   a plurality of nipples distributed along said first edge and along said second edge proximate to said slit, said plurality of nipples extending outwardly from an outer surface of said tube element, and
an expander element comprising:
   an outer member positioned along said outer surface of said tube element, said outer member comprising:
      a plurality of slots arranged diagonally along a longitudinal axis of said outer member, wherein said plurality of nipples extending from said outer surface of said tube element are positioned within, and at, a distal end of a corresponding one of said plurality of slots; and
      an edge covering applied to longitudinal edges of said outer member;
   an inner member positioned along an inner surface of said tube element, and
   a connector positioned between said outer member and said inner member, said connector being positionable within said slit, wherein said expander element is configured to:
      move from an initial position above said proximal end of said tube element toward said distal end of said tube element.

2. The inter-vivos tube of claim 1, further comprising:
an outer flexible membrane encapsulating said tube element, said outer flexible membrane attached proximate to said proximal end of said tube element and extending toward a distal end of said outer member.

3. The inter-vivos tube of claim 1, comprising a distal end cuff element.

4. The inter-vivos tube of claim 3, comprises:
a channel extending toward said distal end cuff element.

5. The inter-vivos tube of claim 1, comprising:
an external pocket, formed on each side of said slit, extending from an outer surface of said tube element, wherein an edge of said outer member is slidable within a corresponding one of said external pockets.

6. The inter-vivos tube of claim 1, comprising:
a channel formed on each side of said slit within said tube element, wherein said outer member is positioned within said channel.

7. The inter-vivos tube of claim 6, comprising:
a channel pocket formed within each of said channels, wherein an edge of said outer member is contained within said pocket.

8. The inter-vivos tube of claim 7, wherein said edge of said outer member is formed to be contained within said channel pocket.

9. The inter-vivos tube of claim 1, comprising:
an optical path between said proximal end of said tube element and said distal end of said tube element.

10. An inter-vivos tube system comprising:
a tube element comprising:
   a longitudinal slit extending from a proximal end of said slit to a distal end of said tube element, and
   a plurality of nipples extending along an outer surface of said tube element proximate to said slit;
an expander extending longitudinally along said outer surface of said tube element, an outer element of said expander comprising:
   a plurality of slots, wherein said plurality of nipples are contained with corresponding ones of said plurality of slots; and
   an edge covering applied to longitudinal edges of said outer element; and
an expansion control comprising:
   a ledge; and
   a diaphragm positioned on a distal end of said expansion control, said diaphragm comprising an opening, wherein said ledge is configured to apply a downward force to a proximal end of said expander to slide said expander downward, wherein said nipples slide within a corresponding one of said plurality of slots from a first position within said corresponding one of said plurality of slots to a second position with said corresponding one of said plurality of slots.

11. The inter-vivos system of claim 10 comprising:
an external pocket formed along an outer surface of said tube element along each side of said slit, wherein an edge of said outer element is positioned within a corresponding one of said external pockets.

12. The inter-vivos tube system of claim 10, comprising:
a channel formed on adjacent each side of said slit, wherein said nipples are formed within said channel and said outer element is positionable within said channel.

13. The inter-vivos tube of claim 12, comprising:
a pocket formed at an edge of said channel, wherein an edge of said outer element is slidable, longitudinally, within said pocket.

14. The inter-vivos tube of claim 13, wherein said edges of said channel are configured to conform to said pocket.

15. An inter-vivos tube comprising:
a tube element comprising:
   a longitudinal slit extending from a proximal end of said tube element to a distal end of said tube element, and
   a plurality of nipples extending from said tube element proximate said slit;
an expander comprising:
   an outer element extending along a surface of said tube element spanning said slit, said outer element extending from said proximal end of said tube element toward said distal end of said tube element, said outer element comprising:
      an edge covering applied to longitudinal edges of said outer element; and
      a plurality of slots arranged diagonally with respect to said longitudinal slit, wherein said plurality of nipples are contained within corresponding ones of said plurality of slots, said outer element configured to:
         slide along said surface toward said distal end of said tube element.

16. The inter-vivos tube of claim 15, comprising:
a plurality of external pockets formed along an outer surface of said tube element, wherein edges of said outer element are slidable within said plurality of said external pockets.

17. The inter-vivos tube of claim 15 comprising:
an expander control positioned along a proximal end of said tube element, said expander control configured to:
apply a force to said expander.

18. The inter-vivos tube of claim 15 comprising:
an outer flexible membrane surrounding said inter-vivos tube.

\* \* \* \* \*